US011413300B2

(12) United States Patent
Jovanovic et al.

(10) Patent No.: US 11,413,300 B2
(45) Date of Patent: Aug. 16, 2022

(54) SYNERGISTIC COMBINATION OF THERMOLYSIN AND AN ANTIBACTERIAL AGENT TO REDUCE OR ELIMINATE BACTERIAL BIOFILMS FROM SURFACES

(71) Applicant: SMITH & NEPHEW, INC., Memphis, TN (US)

(72) Inventors: Aleksa Jovanovic, Fort Worth, TX (US); Lei Shi, Mansfield, TX (US); Eric Roche, Fort Worh, TX (US); Paul Renick, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 237 days.

(21) Appl. No.: 16/481,668

(22) PCT Filed: Jan. 26, 2018

(86) PCT No.: PCT/US2018/015416
§ 371 (c)(1),
(2) Date: Jul. 29, 2019

(87) PCT Pub. No.: WO2018/140707
PCT Pub. Date: Aug. 2, 2018

(65) Prior Publication Data
US 2019/0365791 A1     Dec. 5, 2019

Related U.S. Application Data

(60) Provisional application No. 62/452,203, filed on Jan. 30, 2017.

(51) Int. Cl.
*A61K 31/7036* (2006.01)
*A61K 38/48* (2006.01)
*A61P 31/04* (2006.01)

(52) U.S. Cl.
CPC ...... *A61K 31/7036* (2013.01); *A61K 38/4886* (2013.01); *A61P 31/04* (2018.01); *C12Y 304/24027* (2013.01)

(58) Field of Classification Search
None
See application file for complete search history.

(56) References Cited

U.S. PATENT DOCUMENTS

| | | | |
|---|---|---|---|
| 4,197,291 A | 4/1980 | Klein et al. | |
| 5,902,600 A | 5/1999 | Woller et al. | |
| 6,172,219 B1 | 1/2001 | Callegaro et al. | |
| 6,399,092 B1 | 6/2002 | Hobson et al. | |
| 6,479,060 B1 | 11/2002 | Jones et al. | |
| 6,548,566 B1 | 4/2003 | Hobson et al. | |
| 7,294,497 B2 | 11/2007 | Kaplan | |
| 7,459,155 B2 | 12/2008 | Margolin et al. | |
| 7,642,079 B2 | 1/2010 | Caynouette et al. | |
| 7,785,584 B2 | 8/2010 | Jones et al. | |
| 8,066,991 B2 | 11/2011 | Jolly | |
| 8,119,124 B2 | 2/2012 | Gorecki et al. | |
| 8,383,101 B2 | 2/2013 | Olmstead | |
| 8,632,769 B2 | 1/2014 | Barron | |
| 8,680,072 B2 | 3/2014 | Onsoyen et al. | |
| 8,809,031 B2 | 8/2014 | England et al. | |
| 9,694,100 B2 | 7/2017 | Shi et al. | |
| 10,058,596 B2 | 8/2018 | Hanson | |
| 2003/0026794 A1 | 2/2003 | Fein | |
| 2003/0027310 A1 | 2/2003 | Berka et al. | |
| 2003/0198631 A1* | 10/2003 | Shi .................... | A61K 38/4886 424/94.63 |
| 2003/0198632 A1 | 10/2003 | Shi et al. | |
| 2005/0079594 A1 | 4/2005 | Marion | |
| 2005/0158299 A1 | 7/2005 | Margolin et al. | |
| 2007/0264715 A1 | 11/2007 | Robinson et al. | |
| 2010/0124549 A1 | 5/2010 | Studin | |
| 2010/0221237 A1 | 9/2010 | Kokai-Kun et al. | |
| 2010/0254968 A1 | 10/2010 | Desser et al. | |
| 2012/0258089 A1 | 10/2012 | Madhyastha et al. | |
| 2013/0045196 A1 | 2/2013 | Shi et al. | |
| 2014/0154235 A1 | 6/2014 | Shi et al. | |
| 2015/0118219 A1 | 4/2015 | Shi et al. | |
| 2015/0283217 A1 | 10/2015 | Shi et al. | |
| 2016/0008293 A1 | 1/2016 | Shi et al. | |

(Continued)

FOREIGN PATENT DOCUMENTS

| EP | 0590746 | 4/1994 |
|---|---|---|
| JP | S56-092217 | 7/1981 |

(Continued)

OTHER PUBLICATIONS

Banar, M. et al. Oct. 2016. Evaluation of mannosidsae and trypsin enzymes effects on biofilm production of Pseudomonas aeruginosa isolated from burn wound infections. PLoS One. Oct. 13. pp. 1-13. specif. pp. 1, 2, 3, 4, 7.*
Sugimoto, S. et al. 2013. *Staphylococcus epidermidis* Esp degrades specific proteins associated with *Staphylococcus aureus* biofilm formation and host-pathogen interaction. Journal of Bacteriology 195(8): 1645-1655. specif. pp. 1645, 1646, 1648, 1649.*
Mu, H. et al. Jan. 2016. Potent antibacterial nanoparticles against biofilm and intracellular bacteria. Nature/Scientific Reports 6(18877): 1-9. specif. pp. 1, 3, 4.*
Zhao, G. et al. 2013. Biofilms and inflammation in chronic wounds. Advances in Wound Care 2(7): 389-399. specif. pp. 389, 391, 392.*
Attinger et al., "Clinically Addressing Biofilm in Chronic Wounds" *Advances in Wound Care* 2012, 1(3), pp. 127-132.

(Continued)

*Primary Examiner* — Olivia M. Wise
*Assistant Examiner* — Sharon M. Papciak
(74) *Attorney, Agent, or Firm* — Norton Rose Fulbright US LLP

(57) ABSTRACT

Methods are disclosed for the reduction or elimination of bacterial biofilms on biological and non-biological surfaces, as methods for the treatment of wounds, skin lesions, mucous membrane lesions, and other biological surfaces infected or contaminated with bacterial biofilms using compositions comprising a synergistic combination of thermolysin and at least one aminoglycoside antibacterial agent.

14 Claims, 4 Drawing Sheets

(56) References Cited

U.S. PATENT DOCUMENTS

| | | | |
|---|---|---|---|
| 2018/0289003 | A1 | 10/2018 | Jovanovic et al. |
| 2019/0262437 | A1 | 8/2019 | Shi et al. |

FOREIGN PATENT DOCUMENTS

| | | | |
|---|---|---|---|
| JP | H06-262165 | 9/1994 | |
| JP | 2008-290966 | 12/2008 | |
| JP | 2010-126710 | 6/2010 | |
| WO | WO 02/051436 | 7/2002 | |
| WO | WO 2005/018695 | 3/2005 | |
| WO | WO 2005/047514 | 5/2005 | |
| WO | WO 2005/115357 | 12/2005 | |
| WO | WO 2006/037606 | 4/2006 | |
| WO | WO 2008/019417 | 2/2008 | |
| WO | WO 2009/068841 | 6/2009 | |
| WO | WO 2010/079209 | 7/2010 | |
| WO | WO 2010/112848 | 10/2010 | |
| WO | WO 2011/063394 | 5/2011 | |
| WO | WO 2011/071986 | 6/2011 | |
| WO | WO 2011/163237 | 12/2011 | |
| WO | WO 2012/155027 | 11/2012 | |
| WO | WO 2014/078581 | 5/2014 | |
| WO | WO 2014/145037 | 9/2014 | |
| WO | WO-2015155351 A1 * | 10/2015 | ......... C11D 11/0017 |

OTHER PUBLICATIONS

O'Meara et al., "Antibiotics and antiseptics for venous leg ulcers" *Cochrane Database of Systematic Reviews* 2014, Issue 1, Abstract only, pp. 1-4.
"Research on Microbial Biofilms", National Institutes of Health, PA No. PA-30-047, Dec. 20, 2002, 13 pages.
Ahn et al., "Robust trypsin coating on electrospun polymer nanofibers in rigorous conditions and its uses for protein digestion" *Biotechnol. Bioeng.*, 2010, 107:917-923.
Akiyama et al., "Recent Investigations of *Staphylococcus aureus* in Dermatology" *Japanese Journal of Dermatology*, 1999, 109(13):2095-2102. (English Translation).
Barbera et al., "Multicentre clinical study on seaprose S in acute and chronic respiratory inflammation" *Minuerva Cardioangiol*, 1996,35(4):49-156.
Benedetti, Julia, "Description of Skin Lesions" Merck Manual Professional Version, Feb. 2019, 12 pages.
Bjarnsholt et al., "Why chronic wounds will no heal: a novel hypothesis," *Wound Repair and Regeneration*, 2008, 16:2-10.
Borriello et al., "Oxygen Limitation Contributes to Antibiotic Tolerance of *Pseudomonas aeruginosa* in Biofilms" *Antimicrobial Agents and Chemotherapy*, 2004, 48(7):2659-2664.
Bracale and Selvetella, "Clinical study of the efficacy of and tolerance to seasprose S in inflammatory venous disease. Controlled study versus serration-peptidatse" *Minerva Cardioangiol*, 1996, 44(10):515-524.
Braga et al., "Effects of Seaprose on the Rheology of Bronchial Mucus in Patients with Chronic Bronchitis. A Double-Blind Study vs. Placebo" *Int. J. Clin. Pharm. Res.*, 1993, 8(3):179-185.
Braga et al., "In Vitro Rheological Assessment of Mucolytic Activity Induced by Seaprose" *Pharmacological Research*, 1990, 22(5):611-617.
Braga et al., "The influence of seaprose on erythromycin penetration into bronchial mucux in bronchopulmonary infections," *Drugs Exp. Clin. Res.*, 1992; 18(3):105-111 (Abstract Only).
Das et al., "Attenuation of *Pseudomonas aeruginosa* biofilm formation by Vitexin: A Combinatorial study with azithromycin and gentamicin," *Scientific Reports*, 2016, 6:23347, 13 pages.
Dindelli et al., "Clinical efficacy and safety of Seaprose S in the treatment of surgical wound complications in puerperium" *Minerva Cardioangiol.*, 1990, 42(7-8):313-315.
Drug Information Sheet; Teoase Tablets, 15mg, Revised Mar. 2008, 1 page.
Enzyme Handbook, Springer-Verlag Berlin Heidelber, 1998, pp. 1-8.

Falanga, Vincent "Wound Bed Preparation and the Role of Enzymes: A Case for Multiple Actions of Therapeutic Agents" *Wounds*, 2002, 14(2):47-50.
Fossati, "Antiinflammatory Effects of Seaprose-S on Various Inflammation Models" *Drugs Exptl. Clin. Res.*, 1999, 25(6):263-270.
International Search Report and Written Opinion issued in Corresponding International Patent Application No. PCT/US2018/015416, dated Apr. 17, 2018.
Jacobsen "Investigating the humoral immune response in chronic venous leg ulcer patients colonised with *Pseudomonas aeruginose*" *International Wound Journal*, 2011, 8(1):33-43.
James et al., "Biofilms in Chronic Wounds" *Wound Repair Regen*, 2008, 16:37-44.
Kiedrowski et al., "New approaches for treating staphylococcal biofilm infections" *Ann. N. Y. Acad. Sci.*, 2011, 1241:104-121.
Luisetti et al., "Some Properties of the Alkaline Proteinase From *Aspergillus Melleus*" *Int. J. Tiss. Reac.*, 1991, 13(4):187-192.
Mertz, Patricia, "Cutaneous Biofilms: Friend or Foe?" *Wounds*, 2003, 15(5), 5 pages.
Mingeot-Leclercq et al., "Aminoglycosides: Activity and Resistance," *Antimicrob. Agents. Chemother.*, 1999, 43(4):727-737.
Miyazaki et al., "The Effect of SA-001 (Jeoase) on the Pharyngolaryngeal Complications Following Endotracheal Anesthesia" *Masui (Anesthesia)*, 1969, 18(8):722-730.
Moretti et al., "Effects of Seaprose on Sputum Biochemical Components in Chronic Bronchitic Patients: A Double-Blind Study vs. Placebo" *J. Clin. Phar. Res*, 1993, 8(5):275-280.
Morihara et al., "Comparative study of the various serine alkaline proteinases from microorganisms. Esterase activity against N-acylated peptide ester substrates" *Archives of Biochemistry and Biophysics*, 1974, 165:72-79.
Moro et al., "Atrial natriuretic peptide inhibits the production of adipokines and cytokines linked to inflammation and insulin resistance in human subcutaneous adipose tissue" *Diabetologia*, 2007, 50:1038-1047.
Nakatani et al., "Interaction of Asp. Melleus Semi-Alkaline protease with benzeneboronic acid" *J. Biochem.*, 1972, 81(5): 1269-1272.
Ogawa et al., "The evaluation of the effect of bromelain ointment of the debridement of eschar of burn, decubitus and various wound" *Journal of New Remedies & Clinics*, 1999, 48(10):1301-1309. (English Abstract).
Ohjimi, "Wounds and Infection—Clinical Conditions and Diagnosis of Wounds Infections and Therapeutic Strategies Therefore," *Plastic and Reconstructive Surgery Today*, 2010, 6:1-5.
Polini et al., "Collagen-functionalised electrospun polymer fibers for bioengineering applications" *Soft Matter*, 2010, 6:1668-1674.
Sasaki, Database WPI, Tomson Scientific, XP-002678257, Dec. 4, 2008.
Shi et al., "Evaluation of Wound Debridement Efficacy of Proteolytic Enzymes From the Fungus *Aspergillus melleus*" *Wound Repair and Regeneration*, 2012, 20(2):A39. (Abstract Only).
Spadari et al., "Highly restricted specificity of the serine proteinase aspergillopeptidase B" *Biochimica et Biophysica Acta*, 1974, 359:267-272.
Sugimoto et al., "*Staphylococcus epidermidis* Esp Degrades Specific Proteins Associated with *Staphylococcus aureus* Biofilm Formation and Host-Pathogen Interaction" *Journal of Bacteriology*, 2013, 195(8):1645-1655.
Tiwari, "Burn Wound: How it Differs from Other Wounds?" *Indian Journal of Plastic Surgery*, 2012, 45(2):364-373.
Turkova et al., "Alkaline proteinases of the genus Aspergillus" *Biochimica et Biophysica Acta*, 1972, 257:257-263.
Van der Kar et al., "A Versatile In Vitro Biofilm Model Using Two Wound Pathogens to Screen Formulations," 2010 Wound Healing Society Annual Meeting, Poster BRC09, Apr. 18, 2010.
Williamson et al., "Heterogeneity in *Pseudomonas aeruginosa* Biofilms Includes Expression of Ribosome Hibernation Factors in the Antibiotic-Tolerant Subpopulation and Hypoxia-Induced Stress Response in the Metabolically Active Population," *Journal of Bacteriology*, v2012, 194(8):2062-2073.
Zheng et al., "Penetration of Rifampin through *Staphylococcus epidermidis* Biofilms" *Antimicrobial Agents and Chemotherapy*, 2002, 46(3):900-903.

(56) References Cited

OTHER PUBLICATIONS

"Thermolysin from Geobacillus stearothermophilus." *Sigma-Aldrich*, Feb. 19, 2021, https://www.sigmaaldrich.com/catalog/product/sigma/p1512?lang=en&region=US.

Foster, T. Chapter 12 *Staphylococcus, Medical Microbiology*, 4th Ed., Galveston (TX): University of Texas Medical Branch at Galveston; 1996. (Year: 1996).

Freney et al. "Postoperative infant septicemia caused by Pseudomonas luteola (CDC group Ve-1) and Pseudomonas oryzihabitans (CDC group Ve-2)." *Journal of clinical microbiology*, vol. 26,6 (1988): 1241-3. (Year: 1988).

Page, "Description of Skin Lesions" Merck Manual, 2016, Accessed from the Internet on Jan. 15, 2019, URL <https://www.merckmanuals.com/professional/dermatologic-disorders/approach-to-the-dermatologic-patient/description-of-skin-lesions >.

Scales et al. "Microbiology, genomics, and clinical significance of the Pseudomonas fluorescens species complex, an unappreciated colonizer of humans." *Clinical microbiology reviews* vol. 27,4 (2014): 927-48. (Year: 2014).

Thomas et al. "A Lethal Case of Pseudomonas putida Bacteremia Due to Soft Tissue Infection." *Infectious diseases in clinical practice* (Baltimore, Md.), vol. 21,3 (2013): 147-213. (Year: 2013).

\* cited by examiner

SYNERGISTIC COMBINATION OF THERMOLYSIN AND AN ANTIBACTERIAL AGENT TO REDUCE OR ELIMINATE BACTERIAL BIOFILMS FROM SURFACES

CROSS-REFERENCE WITH RELATED APPLICATIONS

This application is a national phase application under 35 U.S.C. § 371 of International Application No. PCT/US2018/015416, filed Jan. 26, 2018, which claims the benefit of U.S. Provisional Application No. 62/452,203, filed Jan. 30, 2017, the contents of which are incorporated into the present application by reference.

FIELD OF THE INVENTION

The present invention generally relates to methods and compositions useful for reducing or eliminating bacterial biofilms on surfaces. The compositions include thermolysin in combination with an antibacterial agent as active ingredients to reduce or eliminate the bacterial biofilms.

BACKGROUND OF THE INVENTION

Bacterial biofilms are populations of bacteria attached to a surface. Bacteria in a biofilm are frequently embedded within a self-produced matrix of an extracellular polymeric substance (EPS), which holds the bacteria together in a mass and firmly attaches the bacterial mass to the underlying surface. The bacterial biofilm EPS, which is often referred to as slime, is a polymeric conglomeration generally composed of extracellular DNA, proteins, polysaccharides and various biopolymers. Biofilms can form on biological or non-biological surfaces and can be prevalent in both industrial and clinical settings.

Evidence has shown that biofilms constitute a significant threat to human health. Biofilms are responsible for more than 80% of microbial infections in the body ("Research on Microbial Biofilms", National Institutes of Health, PA Number: PA-03-047, Dec. 20, 2002). Biofilms are involved in health conditions such as urinary tract infections, cystitis, lung infections, skin infections, mucous membrane infections, sinus infections, ear infections, acne, dental caries, periodontitis, nosocomial infections, open wounds, and chronic wounds. Additionally, biofilms can form on medical devices such as: urinary tract prostheses; urinary tract catheters; peritoneal membrane catheters, peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses; percutaneous sutures; and tracheal and ventilator tubing.

Bacteria growing in biofilms exhibit increased tolerance to antibiotics and antibacterial agents and are very difficult to substantially reduce or eliminate. Bacteria within biofilms have increased tolerance (up to 1000-fold higher) to antibacterial compounds than bacteria not within biofilms, even though these same bacteria are sensitive to these agents if grown under planktonic conditions ("Research on Microbial Biofilms", National Institutes of Health, PA Number: PA-03-047, Dec. 20, 2002). Bacteria grown in biofilms are also physiologically distinct from the same bacteria grown under planktonic conditions. The bacteria in biofilms are stratified into different metabolic states depending on where in the biofilm they reside and thus display different phenotypes compared to their free-living counterparts. Another theory behind the antimicrobial tolerance of bacteria in biofilms is the protective role of the EPS. The EPS can be visualized as a "mesh" or a network that can physically prevent foreign agents (e.g., antibacterial agents) from reaching the bacteria. Because of the EPS, altered metabolic states and acquired resistance factors, biofilms have a multifactorial tolerance to antibacterial agents and antibiotics. Moreover, many antibacterial formulations are water-based preparations which can, in some instances, make it difficult for the antibacterial active to penetrate the biofilm network due to the high surface tension of water molecules.

Wounds, mucous membrane lesions, and skin lesions are especially susceptible to bacterial infection. From a microbiological perspective, the primary function of normal, intact skin is to control microbial populations that live on the skin surface and to prevent underlying tissue from becoming colonized and invaded by potential pathogens. Exposure of subcutaneous tissue, such as a dermal wound or skin lesion, provides a moist, warm and nutritious environment that is conducive to microbial colonization and proliferation. Since wound colonization is mostly polymicrobial, involving numerous microorganisms that are potentially pathogenic, any wound, mucous membrane lesion, or skin lesion is at some risk of becoming infected.

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment, i.e., a biofilm, following their attachment to a surface, the ability of the host to control these organisms is likely to decrease as the biofilm community matures, ultimately affecting the ability of the wound to heal. Wounds in which healing is delayed, i.e., chronic wounds, are of particular concern with respect to biofilm formation. While biofilms are not present in all bacterial infections, some have linked biofilms to chronic wounds (Mertz, 2003, Wounds, 15: 1-9). Wounds such as diabetic foot ulcers, venous ulcers, arterial ulcers, decubitus ulcers, stasis ulcers, pressure ulcers, and burns are examples of wounds which may become chronic wounds. Bacterial biofilms in chronic wounds are generally not resolved by the host's immune system and these biofilms have an increased tolerance to systemic and topical antibacterial/antibiotic agents. Accordingly, bacterial biofilm infections in chronic wounds are very difficult to substantially reduce or eliminate.

Particularly virulent organisms in wounds, mucous membrane lesions, and skin lesions are gram-positive bacteria such as *Staphylococcus* spp., *Streptococcus* spp., and *Enterococcus* spp. Biofilms of *Staphylococcus aureus*, including resistant strains such as methicillin resistant *Staphylococcus aureus* (MRSA), have become increasingly problematic in wounds, skin lesions, and mucous membrane lesions. These organisms, especially MRSA, can reside in the anterior nares and cause lesions in the nose which can also spread to other parts of the body, causing skin lesions and mucous membrane lesions at those sites. The gram-negative bacteria *Pseudomonas aeruginosa* is also a particularly virulent organism in wounds (Bjarnsholt, 2008, Wound Repair and Regeneration; and Jacobsen, 2011, International Wound Journal).

In recent years, there have been numerous efforts to use various antibiotics and antibacterial agents for the treatment of mucous membrane lesions, skin lesions, and chronic wounds, many of which are infected or contaminated with bacterial biofilms. These agents are of varying chemical compounds and include, among others, antibacterial agents such as mupirocin (and other antibiotics), iodine compounds, and silver/silver ions. However, many bacteria have become increasingly resistant to some antibacterial compounds.

Thus, there is a need for safe and effective compositions which can reduce or eliminate bacterial biofilms in wounds, mucous membrane lesions, and skin lesions, and on other biological and non-biological surfaces.

SUMMARY OF THE INVENTION

The present invention provides a solution to the aforementioned limitations and deficiencies in the art relating to bacterial biofilms. The solution is premised on the combination of thermolysin with an antibacterial agent to reduce or eliminate bacterial biofilms on surfaces, including biological and non-biological surfaces, when administered directly onto the surfaces. In particular, the combination of thermolysin with an aminoglycoside antibacterial agent surprisingly produces a synergistic antibacterial effect against bacterial biofilms. Stated another way, the synergistic effect means the total antibacterial activity against bacterial biofilms of the combination of the two components, i.e., the thermolysin plus the aminoglycoside antibacterial agent, is greater than the sum of the antibacterial activity against biofilms of each component when measured separately. This combination of thermolysin and an aminoglycoside antibacterial agent can be used to produce a composition capable of: treating wounds, mucous membrane lesions, skin lesions, and/or other biological surfaces infected or contaminated with bacterial biofilms; reducing bacteria in and/or eliminating bacterial biofilms on biological surfaces; and/or reducing bacteria in and/or eliminating bacterial biofilms on non-biological surfaces such as on medical devices when the compositions are administered directly onto the surfaces. In preferred embodiments, the aminoglycoside antibacterial agent is a 4,6-disubstituted deoxystreptamine aminoglycoside. Non-limiting examples of aminoglycoside antibacterial agents that are 4,6-disubstituted deoxystreptamine aminoglycosides include kanamycin, amikacin, arbekacin, tobramycin, dibekacin, gentamicin, isepamicin, sisomicin, and netilmicin; and salt forms thereof. In some embodiments, the aminoglycoside antibacterial agent that is a 4,6-disubstituted deoxystreptamine aminoglycoside is gentamicin or a salt form thereof, e.g., gentamicin sulfate. In one instance, the compositions of the present invention can include active agents against biofilms (anti-biofilm active agents that disrupt biofilms) that consist essentially of or consist of only thermolysin and an aminoglycoside antibacterial agent. Stated another way, and in certain embodiments, the compositions of the present invention can include a variety of ingredients but be limited to a combination of thermolysin and an aminoglycoside antibacterial agent as the sole anti-biofilm active agents. In certain other non-limiting aspects, however, the compositions of the present invention can include other anti-biofilm active agents in addition to thermolysin and an aminoglycoside antibacterial agent.

In one aspect of the invention, disclosed is a composition comprising a combination of thermolysin and an aminoglycoside antibacterial agent. In some embodiments, the concentrations of thermolysin and the aminoglycoside antibacterial agent are at amounts effective to reduce or eliminate a bacterial biofilm on a biological and/or a non-biological surface. In some embodiments, the combination of thermolysin and the aminoglycoside antibacterial agent exhibits synergistic antibacterial activity against a bacterial biofilm on a biological and/or a non-biological surface. In preferred embodiments, the aminoglycoside antibacterial agent is a 4,6-disubstituted deoxystreptamine aminoglycoside.

In another aspect of the invention, disclosed is a method for treating a wound, mucous membrane lesion, or skin lesion, infected or contaminated with a bacterial biofilm, the method comprising topically administering to the wound, mucous membrane lesion, or skin lesion a composition comprising a combination of thermolysin and an aminoglycoside antibacterial agent, wherein the bacterial biofilm is reduced or eliminated. In some embodiments, the concentrations of thermolysin and the aminoglycoside antibacterial agent are at amounts effective to reduce or eliminate a bacterial biofilm in a wound, mucous membrane lesion, or skin lesion infected or contaminated with the bacterial biofilm. In some embodiments, the combination of thermolysin and the aminoglycoside antibacterial agent exhibits synergistic antibacterial activity against a bacterial biofilm in a wound, mucous membrane lesion, or skin lesion infected or contaminated with the bacterial biofilm. In preferred embodiments, the aminoglycoside antibacterial agent is a 4,6-disubstituted deoxystreptamine aminoglycoside.

In another aspect of the invention, disclosed is a method of reducing or eliminating a bacterial biofilm on a biological surface, the method comprising administering to the biological surface a composition comprising a combination of thermolysin and an aminoglycoside antibacterial agent. In some embodiments, the concentrations of thermolysin and the aminoglycoside antibacterial agent are at amounts effective to reduce or eliminate a bacterial biofilm on a biological surface. In some embodiments, the combination of thermolysin and the aminoglycoside antibacterial agent exhibits synergistic antibacterial activity against a bacterial biofilm on a biological surface. In preferred embodiments, the aminoglycoside antibacterial agent is a 4,6-disubstituted deoxystreptamine aminoglycoside.

In still another aspect of the invention, disclosed is a method of reducing or eliminating a bacterial biofilm on a non-biological surface, the method comprising administering to the non-biological surface a composition comprising a combination of thermolysin and an aminoglycoside antibacterial agent. In some embodiments, the concentrations of thermolysin and the aminoglycoside antibacterial agent are at amounts effective to reduce or eliminate a bacterial biofilm on a non-biological surface. In some embodiments, the combination of thermolysin and the aminoglycoside antibacterial agent exhibits synergistic antibacterial activity against a bacterial biofilm on a non-biological surface. In preferred embodiments, the aminoglycoside antibacterial agent is a 4,6-disubstituted deoxystreptamine aminoglycoside.

In another aspect of the invention, disclosed is an article of manufacture comprising a surface coated with a composition comprising a combination of thermolysin and an aminoglycoside antibacterial agent. In preferred embodiments, the aminoglycoside antibacterial agent is an aminoglycoside antibacterial agent having 4,6-disubstituted deoxystreptamine.

In another aspect of the invention, disclosed is a method of treating a surface of an article of manufacture to prevent or reduce the likelihood of biofilm formation on said surface, the method comprising coating the surface with a composition comprising a combination of thermolysin and an aminoglycoside antibacterial agent. In preferred embodiments, the aminoglycoside antibacterial agent is an aminoglycoside antibacterial agent having 4,6-disubstituted deoxystreptamine.

In still another aspect of the invention, disclosed is a method for treating a wound infected or contaminated with a bacterial biofilm and in need of debridement, the method comprising topically administering to the wound a composition comprising a combination of thermolysin and an aminoglycoside antibacterial agent, wherein the bacterial biofilm is reduced or eliminated, and wherein the wound is debrided. In some embodiments, the concentrations of thermolysin and the aminoglycoside antibacterial agent are at amounts effective to reduce or eliminate a bacterial biofilm in a wound infected or contaminated with the bacterial biofilm. In some embodiments, the concentration of thermolysin is at an amount effective to debride a wound in need of debridement. In some embodiments, the combination of thermolysin and the aminoglycoside antibacterial agent exhibits synergistic antibacterial activity against a bacterial biofilm in a wound infected or contaminated with the bacterial biofilm. In preferred embodiments, the aminoglycoside antibacterial agent is a 4,6-disubstituted deoxystreptamine aminoglycoside.

In another aspect of the invention, disclosed is a method of reducing or eliminating a bacterial biofilm on a biological surface, the method comprising administering to the biological surface a first composition comprising thermolysin and a second composition comprising an aminoglycoside antibacterial agent, wherein the first and second compositions are combined. In some embodiments, the first and second compositions are combined prior to administration to a biological surface. In other embodiments, the first and second compositions are combined after administration to a biological surface. In some embodiments, the concentrations of thermolysin and the aminoglycoside antibacterial agent are at amounts effective to reduce or eliminate a bacterial biofilm on a biological surface when the first and second compositions are combined. In some embodiments, the combination of the first and second compositions exhibits synergistic antibacterial activity against a biofilm on a biological surface. In preferred embodiments, the aminoglycoside antibacterial agent is a 4,6-disubstituted deoxystreptamine aminoglycoside.

In another aspect of the invention, disclosed is a method of treating a wound, mucous membrane lesion, or skin lesion infected or contaminated with a bacterial biofilm, the method comprising topically administering to the wound, mucous membrane lesion, or skin lesion a first composition comprising thermolysin and a second composition comprising an aminoglycoside antibacterial agent, wherein the first and second compositions are combined, and wherein the bacterial biofilm is reduced or eliminated. In some embodiments, the first and second compositions are combined prior to administration to a wound, mucous membrane lesion, or skin lesion. In other embodiments, the first and second compositions are combined after administration to a wound, mucous membrane lesion, or skin lesion. In some embodiments, the concentrations of thermolysin and the aminoglycoside antibacterial agent are at amounts effective to reduce or eliminate a bacterial biofilm on a wound, mucous membrane lesion, or skin lesion infected or contaminated with the bacterial biofilm when the first and second compositions are combined. In some embodiments, the combination of the first and second compositions exhibits synergistic antibacterial activity against a biofilm on a wound, mucous membrane lesion, or skin lesion infected or contaminated with the bacterial biofilm. In preferred embodiments, the aminoglycoside antibacterial agent is a 4,6-disubstituted deoxystreptamine aminoglycoside.

In still another aspect of the invention, disclosed is a method of treating a wound infected or contaminated with a bacterial biofilm and in need of debridement, the method comprising topically administering to the wound a first composition comprising thermolysin and a second composition comprising an aminoglycoside antibacterial agent, wherein the first and second compositions are combined, wherein the bacterial biofilm is reduced or eliminated, and wherein the wound is debrided. In some embodiments, the first and second compositions are combined prior to administration to a wound. In other embodiments, the first and second compositions are combined after administration to a wound. In some embodiments, the concentrations of thermolysin and the aminoglycoside antibacterial agent are at amounts effective to reduce or eliminate a bacterial biofilm on a wound when the first and second compositions are combined. In some embodiments, the concentration of thermolysin is at an amount effective to debride a wound in need of debridement. In some embodiments, the combination of the first and second compositions exhibits synergistic antibacterial activity against a biofilm on a wound infected or contaminated with the bacterial biofilm. In preferred embodiments, the aminoglycoside antibacterial agent is a 4,6-disubstituted deoxystreptamine aminoglycoside.

In another aspect of the invention, disclosed is a kit comprising (a) a first composition comprising thermolysin, and (b) a second composition comprising an aminoglycoside antibacterial agent. In preferred embodiments, the aminoglycoside antibacterial agent in the second composition is a 4,6-disubstituted deoxystreptamine aminoglycoside. In some embodiments, the kit further comprises instructions for administering the first and second compositions to a biological surface, wound, mucous membrane lesion, and/or skin lesion infected or contaminated with a bacterial biofilm. In some embodiments, the instructions include combining the first and second compositions. In other embodiments, the wound is further in need of debridement.

As disclosed herein, compositions that comprise a combination of thermolysin and gentamicin sulfate (a 4,6-disubstituted deoxystreptamine aminoglycoside) exhibited synergistic antibacterial activity against bacterial biofilms when administered directly onto surfaces that were contaminated with bacterial biofilms. This is an unexpected and surprising result because as the data disclosed herein show, the MIC value of gentamicin sulfate in a bacteria suspension is the same as the MIC value of a combination of gentamicin sulfate and thermolysin in a bacteria suspension. Thus, the addition of thermolysin does not increase the bactericidal effectiveness of gentamicin sulfate against bacteria (not present in a biofilm). This is the case for both gram-positive and gram-negative bacteria. However, the combination of gentamicin sulfate and thermolysin does show a synergistic antibacterial effect when the combination is administered directly onto surfaces contaminated with bacterial biofilms. Stated another way, the total antibacterial activity against bacterial biofilms of the combination of thermolysin and gentamicin sulfate is greater than the sum of the antibacterial activity against bacterial biofilms of each component when measured separately. This is the case for both gram-positive and gram-negative bacterial biofilms. The data also show that thermolysin alone has some antibacterial activity against gram-positive bacterial biofilms, but has little to no antibacterial activity against gram-negative bacterial biofilms. Thus, the synergistic antibacterial effect of the combination of thermolysin and gentamicin sulfate seen on gram-negative bacterial biofilms is even more surprising.

Also disclosed in the context of the present invention are embodiments 1 to 142:

Embodiment 1 is a composition comprising a combination of thermolysin and an aminoglycoside antibacterial agent.

Embodiment 2 is the composition of embodiment 1, wherein the concentrations of thermolysin and the aminoglycoside antibacterial agent are at amounts effective to reduce or eliminate a bacterial biofilm on a biological and/or a non-biological surface.

Embodiment 3 is the composition of embodiment 2, wherein the combination of thermolysin and the aminoglycoside antibacterial agent exhibits synergistic antibacterial activity against the biofilm on the biological and/or the non-biological surface.

Embodiment 4 the composition of any one of embodiments 1 to 3, wherein the aminoglycoside antibacterial agent is a 4,6-disubstituted deoxystreptamine aminoglycoside.

Embodiment 5 is the composition of embodiment 4, wherein the aminoglycoside antibacterial agent is kanamycin, amikacin, arbekacin, tobramycin, dibekacin, gentamicin, isepamicin, sisomicin, or netilmicin; or salt forms thereof.

Embodiment 6 is the composition of embodiment 5, wherein the aminoglycoside antibacterial agent is gentamicin sulfate.

Embodiment 7 is the composition of embodiment 6, wherein the concentration of thermolysin is 0.1 to 1% w/w and the concentration of gentamicin sulfate is equivalent to a concentration of gentamicin of 0.1 to 1% w/w.

Embodiment 8 is the composition of any one of embodiments 1 to 7, wherein the composition further comprises a carrier suitable for application to a biological and/or a non-biological surface.

Embodiment 9 is the composition of embodiment 8, wherein the carrier is a lotion, solution, suspension, liquid, emulsion, cream, gel, ointment, paste, aerosol spray, aerosol foam, non-aerosol spray, non-aerosol foam, film, or sheet.

Embodiment 10 is the composition of embodiment 9, wherein the carrier is suitable for topical administration.

Embodiment 11 is a method of treating a wound, mucous membrane lesion, or skin lesion infected or contaminated with a bacterial biofilm, the method comprising topically administering to the wound, mucous membrane lesion, or skin lesion the composition of any one of embodiments 1 to 10, wherein the bacterial biofilm is reduced or eliminated.

Embodiment 12 is the method of embodiment 11, wherein the bacterial biofilm comprises at least one gram-positive bacterial species.

Embodiment 13 is the method of embodiment 12, wherein the gram-positive bacterial species is a *Staphylococcus* sp.

Embodiment 14 is the method of embodiment 13, wherein the *Staphylococcus* sp. is *Staphylococcus aureus*.

Embodiment 15 is the method of embodiment 13, wherein the *Staphylococcus* sp. is methicillin resistant *Staphylococcus aureus* (MRSA).

Embodiment 16 is the method of embodiment 11, wherein the bacterial biofilm comprises at least one gram-negative bacterial species.

Embodiment 17 is the method of embodiment 16, wherein the gram-negative bacterial species is a *Pseudomonas* sp.

Embodiment 18 is the method of embodiment 17, wherein the *Pseudomonas* sp. is *Pseudomonas aeruginosa*.

Embodiment 19 is the method of embodiment 11, wherein the bacterial biofilm comprises at least one gram-positive bacterial species and at least one gram-negative bacterial species.

Embodiment 20 is the method of any one of embodiments 11 to 19, wherein the wound is a chronic wound, acute wound, or burn.

Embodiment 21 is the method of embodiment 20, wherein the chronic wound is a diabetic foot ulcer, venous ulcer, arterial ulcer, decubitus ulcer, stasis ulcer, or pressure ulcer.

Embodiment 22 is the method of any one of embodiments 11 to 19, wherein the skin lesion or mucous membrane lesion is a blister, ulceration, abrasion, wart, scrape, or infection.

Embodiment 23 is a method of reducing or eliminating a bacterial biofilm on a biological surface, the method comprising administering to the biological surface the composition of any one of embodiments 1 to 10.

Embodiment 24 is the method of embodiment 23, wherein the bacterial biofilm comprises at least one gram-positive bacterial species.

Embodiment 25 is the method of embodiment 24, wherein the gram-positive bacterial species is a *Staphylococcus* sp.

Embodiment 26 is the method of embodiment 25, wherein the *Staphylococcus* sp. is *Staphylococcus aureus*.

Embodiment 27 is the method of embodiment 25, wherein the *Staphylococcus* sp. is methicillin resistant *Staphylococcus aureus* (MRSA).

Embodiment 28 is the method of embodiment 23 wherein the bacterial biofilm comprises at least one gram-negative bacterial species.

Embodiment 29 is the method of embodiment 28, wherein the gram-negative bacterial species is a *Pseudomonas* sp.

Embodiment 30 is the method of embodiment 29, wherein the *Pseudomonas* sp. is *Pseudomonas aeruginosa*.

Embodiment 31 is the method of embodiment 23, wherein the bacterial biofilm comprises at least one gram-positive bacterial species and at least one gram-negative bacterial species.

Embodiment 32 is the method of any one of embodiments 23 to 31, wherein the biological surface is a wound.

Embodiment 33 is the method of embodiment 32, wherein the wound is a chronic wound, acute wound, or burn.

Embodiment 34 is the method of embodiment 33, wherein the chronic wound is a diabetic foot ulcer, venous ulcer, arterial ulcer, decubitus ulcer, stasis ulcer, or pressure ulcer.

Embodiment 35 is the method of any one of embodiments 23 to 31, wherein the biological surface is a skin lesion or mucous membrane lesion.

Embodiment 36 is the method of embodiment 35, wherein the skin lesion or mucous membrane lesion is a blister, ulceration, abrasion, wart, abscess, scrape, or infection.

Embodiment 37 is the method of any one of embodiments 23 to 31, wherein the biological surface is an internal organ, a body cavity, an oral cavity, a bone tissue, a muscle tissue, a nerve tissue, an ocular tissue, a urinary tract tissue, a lung tissue, a trachea tissue, a sinus tissue, an ear tissue, a dental tissue, a gum tissue, a nasal tissue, a vascular tissue, a cardiac tissue, an epithelium tissue, an epithelial lesion, a vaginal tissue, or a peritoneal tissue.

Embodiment 38 is a method of reducing or eliminating a bacterial biofilm on a non-biological surface, the method comprising administering to the non-biological surface the composition of any one of embodiments 1 to 10.

Embodiment 39 is the method of embodiment 38, wherein the non-biological surface is the surface of a medical device.

Embodiment 40 is the method of embodiment 39, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing.

Embodiment 41 is an article of manufacture comprising a surface coated with the composition of any one of embodiments 1 to 10.

Embodiment 42 is the article of manufacture of embodiment 41, wherein the article of manufacture is a medical device.

Embodiment 43 is the article of manufacture of embodiment 42, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing.

Embodiment 44 is the article of manufacture of any one of embodiments 41 to 43, wherein a biofilm is not present on the surface of the article of manufacture prior to coating with the composition.

Embodiment 45 is the article of manufacture of any one of embodiments 41 to 43, wherein a biofilm is present on the surface of the article of manufacture prior to coating the surface with the composition.

Embodiment 46 is a method of treating a surface of an article of manufacture to prevent or reduce the likelihood of biofilm formation on said surface, the method comprising coating the surface with the composition of any one of embodiments 1 to 10.

Embodiment 47 is the method of embodiment 46, wherein the article of manufacture is a medical device.

Embodiment 48 is the method of embodiment 47, wherein the medical device is a urinary tract prosthesis, urinary tract catheter, peritoneal membrane catheter, peritoneal dialysis catheter, indwelling catheter for hemodialysis, indwelling catheter for administration of chemotherapeutic agents, cardiac implant, pacemaker, prosthetic heart valve, ventricular assist device, synthetic vascular graft, synthetic vascular stent, prosthesis, percutaneous suture, tracheal tubing, or ventilator tubing.

Embodiment 49 is a method of treating a wound infected or contaminated with a bacterial biofilm and in need of debridement, the method comprising topically administering to the wound the composition of any one of embodiments 1 to 10, wherein the concentration of thermolysin is at an amount effective to debride the wound, wherein the bacterial biofilm is reduced or eliminated, and wherein the wound is debrided.

Embodiment 50 is the method of embodiment 49, wherein the bacterial biofilm comprises at least one gram-positive bacterial species.

Embodiment 51 is the method of embodiment 50, wherein the gram-positive bacterial species is a *Staphylococcus* sp.

Embodiment 52 is the method of embodiment 51, wherein the *Staphylococcus* sp. is *Staphylococcus aureus*.

Embodiment 53 is the method of embodiment 51, wherein the *Staphylococcus* sp. is methicillin resistant *Staphylococcus aureus* (MRSA).

Embodiment 54 is the method of embodiment 49, wherein the bacterial biofilm comprises at least one gram-negative bacterial species.

Embodiment 55 is the method of embodiment 54, wherein the gram-negative bacterial species is a *Pseudomonas* sp.

Embodiment 56 is the method of embodiment 55, wherein the *Pseudomonas* sp. is *Pseudomonas aeruginosa*.

Embodiment 57 is the method of embodiment 49, wherein the bacterial biofilm comprises at least one gram-positive bacterial species and at least one gram-negative bacterial species.

Embodiment 58 is the method of any one of embodiments 49 to 57, wherein the wound is a chronic wound, acute wound, or burn.

Embodiment 59 is the method of embodiment 58, wherein the chronic wound is a diabetic foot ulcer, venous ulcer, arterial ulcer, decubitus ulcer, stasis ulcer, or pressure ulcer.

Embodiment 60 is a method of reducing or eliminating a bacterial biofilm on a biological surface, the method comprising administering to the biological surface a first composition comprising thermolysin and a second composition comprising an aminoglycoside antibacterial agent, wherein the first and second compositions are combined.

Embodiment 61 is the method of embodiment 60, wherein the first and second compositions are combined prior to administration to the biological surface.

Embodiment 62 is the method of embodiment 60, wherein the first and second compositions are combined after administration to the biological surface.

Embodiment 63 is the method of any of embodiments 60 to 62, wherein the concentrations of thermolysin and the aminoglycoside antibacterial agent are at amounts effective to reduce or eliminate the bacterial biofilm on the biological surface when the first and second compositions are combined.

Embodiment 64 is the method of any one of embodiment 60 to 63, wherein the combination of the first and second compositions exhibits synergistic antibacterial activity against the biofilm on the biological surface.

Embodiment 65 is the method of any one of embodiments 60 to 64, wherein the aminoglycoside antibacterial agent is a 4,6-disubstituted deoxystreptamine aminoglycoside.

Embodiment 66 is the method of embodiment 65, wherein the aminoglycoside antibacterial agent is kanamycin, amikacin, arbekacin, tobramycin, dibekacin, gentamicin, isepamicin, sisomicin, or netilmicin; or salt forms thereof.

Embodiment 67 is the method of embodiment 66, wherein the aminoglycoside antibacterial agent is gentamicin sulfate.

Embodiment 68 is the method of embodiment 67, wherein the concentration of thermolysin is 0.1 to 1% w/w and the concentration of gentamicin sulfate is equivalent to a concentration of gentamicin of 0.1 to 1% w/w.

Embodiment 69 is the method of any one of embodiments 60 to 68, wherein the first composition and the second composition further comprises a carrier suitable for application to a biological surface.

Embodiment 70 is the method of embodiment 69, wherein the carrier is a lotion, solution, suspension, liquid, emulsion, cream, gel, ointment, paste, aerosol spray, aerosol foam, non-aerosol spray, non-aerosol foam, film, or sheet.

Embodiment 71 is the method of embodiment 70, wherein the carrier is suitable for topical administration.

Embodiment 72 is the method of any of embodiments 60 to 71, wherein the bacterial biofilm comprises at least one gram-positive bacterial species.

Embodiment 73 is the method of embodiment 72, wherein the gram-positive bacterial species is a *Staphylococcus* sp.

Embodiment 74 is the method of embodiment 73, wherein the *Staphylococcus* sp. is *Staphylococcus aureus*.

Embodiment 75 is the method of embodiment 73, wherein the *Staphylococcus* sp. is methicillin resistant *Staphylococcus aureus* (MRSA).

Embodiment 76 is the method of any one of embodiments 60 to 71, wherein the bacterial biofilm comprises at least one gram-negative bacterial species.
Embodiment 77 is the method of embodiment 76, wherein the gram-negative bacterial species is a *Pseudomonas* sp.
Embodiment 78 is the method of embodiment 77, wherein the *Pseudomonas* sp. is *Pseudomonas aeruginosa*.
Embodiment 79 is the method of any one of embodiments 60 to 71, wherein the bacterial biofilm comprises at least one gram-positive bacterial species and at least one gram-negative bacterial species.
Embodiment 80 is the method of any one of embodiments 60 to 79, wherein the biological surface is a wound.
Embodiment 81 is the method of embodiment 80, wherein the wound is a chronic wound, acute wound, or burn.
Embodiment 82 is the method of embodiment 81, wherein the chronic wound is a diabetic foot ulcer, venous ulcer, arterial ulcer, decubitus ulcer, stasis ulcer, or pressure ulcer.
Embodiment 83 is the method of any one of embodiments 60 to 79, wherein the biological surface is a skin lesion or mucous membrane lesion.
Embodiment 84 is the method of embodiment 83, wherein the skin lesion or mucous membrane lesion is a blister, ulceration, abrasion, wart, abscess, scrape, or infection.
Embodiment 85 is the method of any one of embodiments 60 to 79, wherein the biological surface is an internal organ, a body cavity, an oral cavity, a bone tissue, a muscle tissue, a nerve tissue, an ocular tissue, a urinary tract tissue, a lung tissue, a trachea tissue, a sinus tissue, an ear tissue, a dental tissue, a gum tissue, a nasal tissue, a vascular tissue, a cardiac tissue, an epithelium tissue, an epithelial lesion, a vaginal tissue, or a peritoneal tissue.
Embodiment 86 is a method of treating a wound, mucous membrane lesion, or skin lesion infected or contaminated with a bacterial biofilm, the method comprising topically administering to the wound, mucous membrane lesion, or skin lesion a first composition comprising thermolysin and a second composition comprising an aminoglycoside antibacterial agent, wherein the first and second compositions are combined, and wherein the bacterial biofilm is reduced or eliminated.
Embodiment 87 is the method of embodiment 86, wherein the first and second compositions are combined prior to administration to the wound, mucous membrane lesion, or skin lesion.
Embodiment 88 is the method of embodiment 86, wherein the first and second compositions are combined after administration to the wound, mucous membrane lesion, or skin lesion.
Embodiment 89 is the method of any of embodiments 86 to 88, wherein the concentrations of thermolysin and the aminoglycoside antibacterial agent are at amounts effective to reduce or eliminate the bacterial biofilm on the wound, mucous membrane lesion, or skin lesion when the first and second compositions are combined.
Embodiment 90 is the method of any one of embodiments 86 to 89, wherein the combination of the first and second compositions exhibits synergistic antibacterial activity against the biofilm on the wound, mucous membrane lesion, or skin lesion.
Embodiment 91 is the method of any one of embodiments 86 to 90, wherein the aminoglycoside antibacterial agent is a 4,6-disubstituted deoxystreptamine aminoglycoside.
Embodiment 92 is the method of embodiment 91, wherein the aminoglycoside antibacterial agent is kanamycin, amikacin, arbekacin, tobramycin, dibekacin, gentamicin, isepamicin, sisomicin, or netilmicin; or salt forms thereof.

Embodiment 93 is the method of embodiment 92, wherein the aminoglycoside antibacterial agent is gentamicin sulfate.
Embodiment 94 is the method of embodiment 93, wherein the concentration of thermolysin is 0.1 to 1% w/w and the concentration of gentamicin sulfate is equivalent to a concentration of gentamicin of 0.1 to 1% w/w.
Embodiment 95 is the method of any one of embodiments 86 to 94, wherein the first composition and the second composition further comprises a carrier suitable for topical administration.
Embodiment 96 is the method of embodiment 95, wherein the carrier is a lotion, solution, suspension, liquid, emulsion, cream, gel, ointment, paste, aerosol spray, aerosol foam, non-aerosol spray, non-aerosol foam, film, or sheet.
Embodiment 97 is the method of any one of embodiment 86 to 96, wherein the bacterial biofilm comprises at least one gram-positive bacterial species.
Embodiment 98 is the method of embodiment 97, wherein the gram-positive bacterial species is a *Staphylococcus* sp.
Embodiment 99 is the method of embodiment 98, wherein the *Staphylococcus* sp. is *Staphylococcus aureus*.
Embodiment 100 is the method of embodiment 98, wherein the *Staphylococcus* sp. is methicillin resistant *Staphylococcus aureus* (MRSA).
Embodiment 101 is the method of any one of embodiments 86 to 96, wherein the bacterial biofilm comprises at least one gram-negative bacterial species.
Embodiment 102 is the method of embodiment 101, wherein the gram-negative bacterial species is a *Pseudomonas* sp.
Embodiment 103 is the method of embodiment 102, wherein the *Pseudomonas* sp. is *Pseudomonas aeruginosa*.
Embodiment 104 is the method of any one of embodiments 86 to 96, wherein the bacterial biofilm comprises at least one gram-positive bacterial species and at least one gram-negative bacterial species.
Embodiment 105 is the method of any one of embodiments 86 to 104, wherein the wound is a chronic wound, acute wound, or burn.
Embodiment 106 is the method of embodiment 105, wherein the chronic wound is a diabetic foot ulcer, venous ulcer, arterial ulcer, decubitus ulcer, stasis ulcer, or pressure ulcer.
Embodiment 107 is the method of any one of embodiments 86 to 104, wherein the skin lesion or mucous membrane lesion is a blister, ulceration, abrasion, wart, scrape, or infection.
Embodiment 108 is a method of treating a wound infected or contaminated with a bacterial biofilm and in need of debridement, the method comprising topically administering to the wound a first composition comprising thermolysin and a second composition comprising an aminoglycoside antibacterial agent, wherein the first and second compositions are combined, wherein the bacterial biofilm is reduced or eliminated, and wherein the wound is debrided.
Embodiment 109 is the method of embodiment 108, wherein the first and second compositions are combined prior to administration to the wound.
Embodiment 110 is the method of embodiment 108, wherein the first and second compositions are combined after administration to the wound.
Embodiment 111 is the method of any of embodiments 108 to 110, wherein the concentrations of thermolysin and the aminoglycoside antibacterial agent are at amounts effective to reduce or eliminate the bacterial biofilm on the wound when the first and second compositions are combined.
Embodiment 112 is the method of any of embodiments 108 to 110, wherein the concentration of thermolysin is at an amount effective to debride the wound.

Embodiment 113 is the method of any one of embodiments 108 or 112, wherein the combination of the first and second compositions exhibits synergistic antibacterial activity against the biofilm on the wound.

Embodiment 114 is the method of any one of embodiments 108 to 113, wherein the aminoglycoside antibacterial agent is a 4,6-disubstituted deoxystreptamine aminoglycoside.

Embodiment 115 is the method of embodiment 114, wherein the aminoglycoside antibacterial agent is kanamycin, amikacin, arbekacin, tobramycin, dibekacin, gentamicin, isepamicin, sisomicin, or netilmicin; or salt forms thereof.

Embodiment 116 is the method of embodiment 115, wherein the aminoglycoside antibacterial agent is gentamicin sulfate.

Embodiment 117 is the method of embodiment 116, wherein the concentration of thermolysin is 0.1 to 1% w/w and the concentration of gentamicin sulfate is equivalent to a concentration of gentamicin of 0.1 to 1% w/w.

Embodiment 118 is the method of any one of embodiments 108 to 117, wherein the first composition and the second composition further comprises a carrier suitable for topical administration.

Embodiment 119 is the method of embodiment 118, wherein the carrier is a lotion, solution, suspension, liquid, emulsion, cream, gel, ointment, paste, aerosol spray, aerosol foam, non-aerosol spray, non-aerosol foam, film, or sheet.

Embodiment 120 is the method of any one of embodiments 108 to 119, wherein the bacterial biofilm comprises at least one gram-positive bacterial species.

Embodiment 121 is the method of embodiment 120, wherein the gram-positive bacterial species is a *Staphylococcus* sp.

Embodiment 122 is the method of embodiment 121, wherein the *Staphylococcus* sp. is *Staphylococcus aureus*.

Embodiment 123 is the method of embodiment 121, wherein the *Staphylococcus* sp. is methicillin resistant *Staphylococcus aureus* (MRSA).

Embodiment 124 is the method of any one of embodiments 108 to 119, wherein the bacterial biofilm comprises at least one gram-negative bacterial species.

Embodiment 125 is the method of embodiment 124, wherein the gram-negative bacterial species is a *Pseudomonas* sp.

Embodiment 126 is the method of embodiment 125, wherein the *Pseudomonas* sp. is *Pseudomonas aeruginosa*.

Embodiment 127 is the method of any one of embodiments 108 to 119, wherein the bacterial biofilm comprises at least one gram-positive bacterial species and at least one gram-negative bacterial species.

Embodiment 128 is the method of any one of embodiments 108 to 127, wherein the wound is a chronic wound, acute wound, or burn.

Embodiment 129 is the method of embodiment 128, wherein the chronic wound is a diabetic foot ulcer, venous ulcer, arterial ulcer, decubitus ulcer, stasis ulcer, or pressure ulcer.

Embodiment 130 is a kit comprising:
  (a) a first composition comprising thermolysin, and
  (b) a second composition comprising an aminoglycoside antibacterial agent.

Embodiment 131 is the kit of embodiment 130, wherein the aminoglycoside antibacterial agent is a 4,6-disubstituted deoxystreptamine aminoglycoside.

Embodiment 132 is the kit of embodiment 131, wherein the aminoglycoside antibacterial agent is kanamycin, amikacin, arbekacin, tobramycin, dibekacin, gentamicin, isepamicin, sisomicin, or netilmicin; or salt forms thereof.

Embodiment 133 is the kit of embodiment 132, wherein the aminoglycoside antibacterial agent is gentamicin sulfate.

Embodiment 134 is the kit of embodiment 133, wherein the concentration of thermolysin is 0.1 to 1% w/w and the concentration of gentamicin sulfate is equivalent to a concentration of gentamicin of 0.1 to 1% w/w.

Embodiment 135 is the kit of any one of embodiments 130 to 134, wherein the first composition and the second composition further comprise a carrier suitable for application to a biological surface.

Embodiment 136 is the kit of embodiment 135, wherein the carrier is a lotion, solution, suspension, liquid, emulsion, cream, gel, ointment, paste, aerosol spray, aerosol foam, non-aerosol spray, non-aerosol foam, film, or sheet.

Embodiment 137 is the kit of embodiment 136, wherein the carrier is suitable for topical administration.

Embodiment 138 is the kit of any one of embodiments 130 to 137, further comprising instructions for administering the first and second compositions to a biological surface, wound, mucous membrane lesion, and/or skin lesion; wherein the wound, mucous membrane lesion, and/or skin lesion is infected or contaminated with a bacterial biofilm.

Embodiment 139 is the kit of embodiment 138, wherein the instructions include combining the first and second compositions.

Embodiment 140 is the kit of embodiment 139, wherein the instructions include combining the first and second compositions prior to administration to the wound, mucous membrane lesion, and/or skin lesion.

Embodiment 141 is the kit of embodiment 139, wherein the instructions include combining the first and second compositions after administration to the wound, mucous membrane lesion, and/or skin lesion.

Embodiment 142 is the kit of any one of embodiments 138 to 141, wherein the wound is further in need of debridement.

Unless otherwise specified, the percent values expressed herein are weight by weight and are in relation to the weight of the total composition. By way of example, 10 grams of component in 100 grams of material is 10% w/w of component.

For purposes of this application, a number value with one or more decimal places can be rounded to the nearest whole number using standard rounding guidelines, i.e. round up if the number being rounded is 5, 6, 7, 8, or 9; and round down if the number being rounded is 0, 1, 2, 3, or 4. For example, 0.42 can be rounded to 0.4.

The terms "reduce", "reduced", "reducing", or "reduction" in the context of a bacterial biofilm means a reduction in the count of bacteria in the biofilm.

The terms "treat," "treated," "treatment", or "treating," in the context of treating a bacterial biofilm on a biological surface, or treating a mucous membrane lesion, a wound, or a skin lesion, means any measurable reduction or complete elimination of the bacterial biofilm, and/or a therapeutic improvement of the mucous membrane lesion, wound, or skin lesion.

The term "effective," in the context of treating a bacterial biofilm or treating a wound, mucous membrane lesion, or skin lesion means adequate to accomplish a desired, expected, or intended result, including a therapeutic improvement.

The terms "eliminate", "eliminated", "eliminating", or "elimination" in the context of a bacterial biofilm means total eradication of the bacteria present in the biofilm.

The terms "prevent", "prevented", or "preventing" in the context of a bacterial biofilm means reduced likelihood or complete prevention of bacterial biofilm formation on a surface such as a biological or a non-biological surface that has been coated with a composition of the present invention.

The term "wound" as used herein means an external wound of the skin or mucous membranes and includes chronic and acute wounds.

The term "lesion" as used herein means a region on a bodily tissue that has suffered damage through injury or disease.

As used herein, the terms "administer", "administration", "administering" in the context of applying a composition to a biological surface means physically placing the composition directly onto the surface, i.e., not systemic, intravenous, or oral administration.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising", "having", "including", or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the ability of the combination of thermolysin and an aminoglycoside antibacterial agent to disrupt bacterial biofilms.

It is contemplated that any embodiment discussed in this specification can be implemented with respect to any method or composition of the invention, and vice versa.

Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
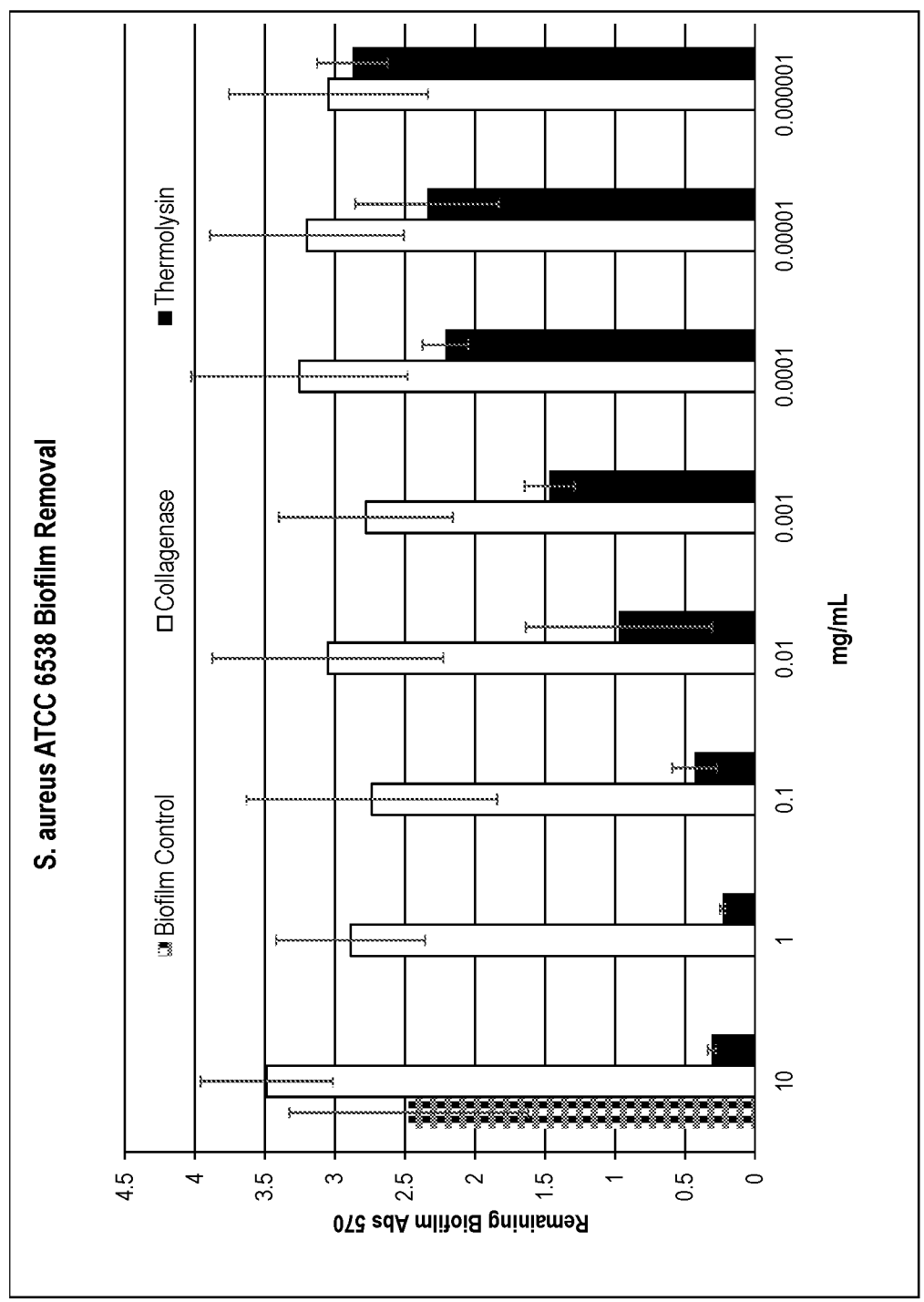
FIG. 1. A graph showing the effect of thermolysin and collagenase on a S. aureus bacterial biofilm in-vitro.

The present invention relates to methods and compositions useful for the reduction, elimination, or prevention of bacterial biofilms and/or growth of such biofilms on surfaces. In particular, the present invention provides compositions comprising a combination of thermolysin and an aminoglycoside antibacterial agent which surprisingly exhibit synergistic antibacterial activity against bacterial biofilms when administered directly onto surfaces contaminated with bacterial biofilms. The present invention also provides methods of administering these compositions to biological and non-biological surfaces infected or contaminated with bacterial biofilms thereby effectively reducing or eliminating the bacterial biofilms. In preferred embodiments, the aminoglycoside antibacterial agent is an aminoglycoside antibacterial agent that is a 4,6-disubstituted deoxystreptamine aminoglycoside. In some preferred embodiments, the 4,6-disubstituted deoxystreptamine aminoglycoside is gentamicin or gentamicin sulfate.

Additionally, surfaces susceptible to biofilm formation (e.g., medical devices) can be treated with such compositions to prevent biofilm formation. In one aspect, the present invention relates to methods and compositions useful for the treatment of wounds, skin lesions, mucous membrane lesions, and other biological surfaces infected or contaminated with bacterial biofilms. In another aspect, the present invention relates to methods and compositions useful for the reduction, elimination, and/or prevention of bacterial biofilms and/or growth of such biofilms on non-biological surfaces such as medical devices.

I. Compositions

The compositions of the present invention comprise a combination of thermolysin and an aminoglycoside antibacterial agent. In preferred embodiments, the aminoglycoside antibacterial agent is an aminoglycoside antibacterial agent having 4,6-disubstituted deoxystreptamine. In a preferred embodiment, the 4,6-disubstituted deoxystreptamine aminoglycoside is gentamicin or gentamicin sulfate. The compositions surprisingly exhibit synergistic antibacterial activity against both gram-positive and gram-negative bacterial biofilms.

A. Thermolysin

Thermolysin is a thermostable metalloproteinase made by a fermentation process from a bacterial species called *Bacillus thermoproteolyticus* rokko that cleaves at the N-terminus of the hydrophobic residues leucine, phenylalanine, valine, isoleucine, alanine, and methionine. Amano Japan is a manufacturer and commercial supplier of thermolysin. The thermolysin can be isolated and/or purified. The CAS No. for thermolysin is 9073-78-3.

B. Aminoglycoside Antibacterial Agents

Aminoglycoside antibacterial agents (aminoglycosides) are a group of antibacterial therapeutic agents (antibiotics) that act by inhibiting bacterial protein synthesis and contain an amino-modified glycoside. Aminoglycoside antibacterial agents act primarily by impairing bacterial protein synthesis by binding to cytosolic bacterial ribosomes. In the cytosol, aminoglycosides bind to the 30S subunit of ribosomes and perturb the elongation of the nascent chain by impairing the proofreading process controlling translational accuracy (misreading and/or premature termination) (Mingeot-Leclercq et al, Aminoglycosides: Activity and Resistance, Antimicrob Agents Chemother, 1999, April, 43(4), 727-737). The basic chemical structure of an aminoglycoside antibacterial agent has one or more aminated sugars joined in glycosidic linkages to a dibasic cyclitol. The aminoglycoside antibacterial agents are classified into two classes: those containing 2-deoxystreptamine and those that do not contain 2-deoxystreptamine. In the class of aminoglycoside antibacterial agents containing 2-deoxystreptamine, there are two sub-classes: 4,6-disubstituted deoxystreptamine aminoglycosides and 4,5-disubstituted deoxystreptamine aminoglycosides. Non-limiting examples of aminoglycoside antibacterial agents that are 4,6-disubstituted deoxystreptamine aminoglycosides include kanamycin (including kanamycin A, B, and/or C), amikacin, arbekacin, tobramycin, dibekacin, gentamicin (including gentamicins C1, C1a, C2, C2a, and/or C2b), isepamicin, sisomicin, and netilmicin; and salt forms thereof. Non-limiting examples of aminoglycoside antibacterial agents that are 4,5-disubstituted deoxystreptamine aminoglycosides include neomycin (including neomycin A, B, and C), paromomycin (including paromomycin I), lividomycin (including lividomycin A), ribostamycin and butirosin (including butirosin B); and salt forms thereof. Non-limiting examples of the class of aminoglycoside antibacterial agents that do not contain 2-deoxystreptamine include streptomycin, dihydrostreptomycin, fortimicin A, dactimicin, and apramycin; and salt forms thereof.

In some embodiments, the aminoglycoside antibacterial agent is an aminoglycoside antibacterial agent that does not contain 2-deoxystreptamine. In some embodiments, the aminoglycoside antibacterial agent that does not contain 2-deoxystreptamine is streptomycin, dihydrostreptomycin, fortimicin A, dactimicin, or apramycin; or salt forms thereof. In some embodiments, the aminoglycoside antibacterial agent is an aminoglycoside antibacterial agent that contains 2-deoxystreptamine. In other embodiments, the aminoglycoside antibacterial agent is a 4,5-disubstituted deoxystreptamine aminoglycoside. In some embodiments, the aminoglycoside antibacterial agent that is a 4,5-disubstituted deoxystreptamine aminoglycoside is neomycin, paromomycin, lividomycin, ribostamycin, or butirosin; or salt forms thereof. In preferred embodiments, the aminoglycoside antibacterial agent is a 4,6-disubstituted deoxystreptamine aminoglycoside. In preferred embodiments, the aminoglycoside antibacterial agent that is a 4,6-disubstituted deoxystreptamine aminoglycoside is kanamycin, amikacin, arbekacin, tobramycin, dibekacin, gentamicin, isepamicin, sisomicin, or netilmicin; or salt forms thereof. In a preferred embodiment, the aminoglycoside antibacterial agent that is a 4,6-disubstituted deoxystreptamine aminoglycoside is gentamicin or a salt form thereof, e.g., gentamicin sulfate.

Gentamicin (and its salt form gentamicin sulfate) is a member of the subclass of aminoglycoside antibacterial agents that are 4,6-disubstituted deoxystreptamine aminoglycosides. The CAS No. for gentamicin is 1403-66-3. The CAS No. for gentamicin sulfate is 1405-41-0. Gentamicin is produced by the fermentation of *Micromonospora purpurea* and is defined as a complex of related gentamicin components. Such components include gentamicin C1, gentamicin C1a, gentamicin C2, gentamicin C2a, and/or gentamicin C2b. The sulfate salt of gentamicin, gentamicin sulfate, is commonly used as an antibacterial therapeutic agent in pharmaceutical preparations. Topical gentamicin sulfate creams (0.1%) and ointments (0.1%) are available in the US as prescription medications and contain gentamicin sulfate at an amount equivalent to 0.1% w/w gentamicin. Ophthalmic gentamicin sulfate drops and ointments (0.3%. 0.6%, and 1%) are also available in the US as prescription medications. Gentamicin sulfate is a mixture of sulfate salts of related gentamicin components which include C1, C1a, C2, C2a, and/or C2b. Gentamicin sulfate is shown in Formula I and the related gentamicin components are described in Table 1 corresponding to R1, R2, and R3 of Formula I.

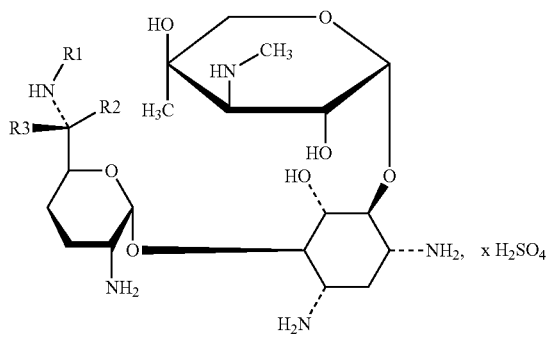

Formula I

TABLE 1

| Gentamicin component | R1 | R2 | R3 |
|---|---|---|---|
| C1 | CH₃ | CH₃ | H |
| C1a | H | H | H |
| C2 | H | CH₃ | H |
| C2a | H | H | CH₃ |
| C2b | CH₃ | H | H |

The USP monograph for gentamicin sulfate (USP 31) measures the content of the related gentamicin components C1, C1a, C2, and C2a with the following limits: gentamicin C1 between 25% to 50%; gentamicin C1a between 10% to 35%; and the sum of gentamicins C2 and C2a between 25% to 55%. The European Pharmacopoeia (Ph. Eur.) monograph 0331 for gentamicin sulphate measures the content of the related gentamicin components C1, C1a, C2, C2a, and C2b with the following limits: gentamicin C1 is from 20.0% to 40.0%; gentamicin C1a is from 10.0% to 30%; and the sum of gentamicins C2, C2a, and C2b is from 40.0% to 60.0%. Both the USP and Ph. Eur. grades of gentamicin sulfate have a potency of not less than 590 μg of gentamicin per mg, calculated on the dried basis. The Ph. Eur. grade of gentamicin sulfate has a maximum limit of 15% water, and the USP grade has a loss on drying limit of not more than 18.0%. USP and Ph. Eur. grades of gentamicin sulfate are suitable grades for use in the compositions of the invention.

The concentrations of the thermolysin and the aminoglycoside antibacterial agent in the composition are at amounts that produce a synergistic antibacterial effect against bacterial biofilms and are effective at reducing or eliminating a bacterial biofilm on a biological and/or a non-biological surface. The concentrations of thermolysin and/or the aminoglycoside antibacterial agent can vary depending on the specific aminoglycoside antibacterial agent used in the compositions. Further, and as noted in other parts of the specification, certain embodiments of the present invention contemplate limiting the anti-biofilm active agents present in the compositions to thermolysin and an aminoglycoside antibacterial agent (e.g., gentamicin or a salt thereof such as gentamicin sulfate).

In various embodiments, the concentration of the aminoglycoside antibacterial agent is 0.01 to 10% w/w, or 0.01 to 5% w/w, or 0.01 to 4% w/w, or 0.01 to 3% w/w, or 0.01 to 2% w/w, or 0.01 to 1.5% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.01 to 0.3% w/w, or 0.01 to 0.2% w/w, or 0.01 to 0.1% w/w, or 0.01 to 0.05% w/w, or 0.05 to 10% w/w, or 0.05 to 5% w/w, or 0.05 to 4% w/w, or 0.05 to 3% w/w, or 0.05 to 2% w/w, or 0.05 to 1.5% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.05 to 0.3% w/w, or 0.05 to 0.2% w/w, or 0.05 to 0.15% w/w, or 0.05 to 0.1% w/w, or 0.1 to 10% w/w, or 0.1 to 5% w/w, or 0.1 to 4% w/w, or 0.1 to 3% w/w, or 0.1 to 2% w/w, or 0.1 to 1.5% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.1 to 0.2% w/w, or 0.2 to 10% w/w, or 0.2 to 5% w/w, or 0.2 to 4% w/w, or 0.2 to 3% w/w, or 0.2 to 2% w/w, or 0.2 to 1.5% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.3 to 10% w/w, or 0.3 to 5% w/w, or 0.3 to 4% w/w, or 0.3 to 3% w/w, or 0.3 to 2% w/w, or 0.3 to 1.5% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w.

In various embodiments where gentamicin sulfate is used in the compositions, the amount of gentamicin sulfate in the compositions is equivalent to a gentamicin concentration of: 0.01 to 10% w/w, or 0.01 to 5% w/w, or 0.01 to 4% w/w, or 0.01 to 3% w/w, or 0.01 to 2% w/w, or 0.01 to 1.5% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.01 to 0.3% w/w, or 0.01 to 0.2% w/w, or 0.01 to 0.1% w/w, or 0.01 to 0.05% w/w, or 0.05 to 10% w/w, or 0.05 to 5% w/w, or 0.05 to 4% w/w, or 0.05 to 3% w/w, or 0.05 to 2% w/w, or 0.05 to 1.5% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.05 to 0.3% w/w, or 0.05 to 0.2% w/w, or 0.05 to 0.15% w/w, or 0.05 to 0.1% w/w, or 0.1 to 10% w/w, or 0.1 to 5% w/w, or 0.1 to 4% w/w, or 0.1 to 3% w/w, or 0.1 to 2% w/w, or 0.1 to 1.5% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.1 to 0.2% w/w, or 0.2 to 10% w/w, or 0.2 to 5% w/w, or 0.2 to 4% w/w, or 0.2 to 3% w/w, or 0.2 to 2% w/w, or 0.2 to 1.5% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.3 to 10% w/w, or 0.3 to 5% w/w, or 0.3 to 4% w/w, or 0.3 to 3% w/w, or 0.3 to 2% w/w, or 0.3 to 1.5% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w.

In various embodiments, the concentration of thermolysin is 0.01 to 10% w/w, or 0.01 to 5% w/w, or 0.01 to 4% w/w, or 0.01 to 3% w/w, or 0.01 to 2% w/w, or 0.01 to 1.5% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.01 to 0.3% w/w, or 0.01 to 0.2% w/w, or 0.01 to 0.1% w/w, or 0.01 to 0.05% w/w, or 0.05 to 10% w/w, or 0.05 to 5% w/w, or 0.05 to 4% w/w, or 0.05 to 3% w/w, or 0.05 to 2% w/w, or 0.05 to 1.5% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.05 to 0.3% w/w, or 0.05 to 0.2% w/w, or 0.05 to 0.15% w/w, or 0.05 to 0.1% w/w, or 0.1 to 10% w/w, or 0.1 to 5% w/w, or 0.1 to 4% w/w, or 0.1 to 3% w/w, or 0.1 to 2% w/w, or 0.1 to 1.5% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.1 to 0.2% w/w, or 0.2 to 10% w/w, or 0.2 to 5% w/w, or 0.2 to 4% w/w, or 0.2 to 3% w/w, or 0.2 to 2% w/w, or 0.2 to 1.5% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.3 to 10% w/w, or 0.3 to 5% w/w, or 0.3 to 4% w/w, or 0.3 to 3% w/w, or 0.3 to 2% w/w, or 0.3 to 1.5% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w.

In a preferred example, the composition comprises 0.80% w/w thermolysin and 0.70% w/w gentamicin sulfate USP (as-is basis) equivalent to 0.42% w/w gentamicin.

C. Carriers and Adjuvants

The compositions of the invention can comprise an acceptable carrier such as a carrier suitable for application to biological surfaces including wounds, mucous membranes, skin, organs and other biological tissues; or a carrier suitable for application to non-biological surfaces including medical devices. The carrier can be a pharmaceutically acceptable carrier. The carrier can be a carrier suitable for topical administration and treatment. Non-limiting examples of carriers include lotions, solutions, suspensions, liquids, emulsions, creams, gels, ointments, pastes, aerosol sprays, aerosol foams, non-aerosol sprays, non-aerosol foams, films, powders, and sheets. The compositions can be impregnated in gauzes, bandages, or other wound and skin dressing materials. Non-limiting examples of carriers suitable for topical treatment of skin, mucous membranes and wounds include those carriers disclosed in U.S. Pat. No. 6,399,092, herein incorporated by reference, which are anhydrous, hydrophilic carriers comprising a super absorbent polymer, an antimicrobial agent, and poloxamers and/or polyols. The carriers disclosed in US publication 2016/0008293, herein incorporated by reference, which are dissolvable gel-forming film compositions with a water content of less than 15% w/w comprising a water-soluble cellulose ether, a hydrophilic rheological modifying agent, and a proteolytic enzyme, wherein the gel-forming film is capable of forming a hydrogel when in contact with water or other aqueous medium, are suitable carriers for topical treatment of skin, mucous membranes, and wounds. The carriers disclosed in US publication 2013/0045196, herein incorporated by reference, which are compositions comprising a dispersed phase comprising a liquid hydrophilic polyol and a proteolytic enzyme, and a continuous phase comprising a hydrophobic base, are suitable carriers for topical treatment of skin, mucous membranes, and wounds. The carriers disclosed in US publication 2015/0283217, herein incorporated by reference, which are hydrogel compositions comprising a hydrophilic gelling agent that includes a nonionic cellulose ether and thermolysin, are suitable carriers for topical treatment of skin, mucous membranes, and wounds. The carriers disclosed in U.S. Pat. No. 7,785,584, herein incorporated by reference, which are spray-on compositions comprising a cryptoanionic surfactant emulsifier comprising an alkoxylated fatty alcohol and mono and diester phosphates; at least one wound healing agent, emollient, humectant, preservative, or anti-microbial; and a proteolytic enzyme; are suitable carriers for topical treatment of skin, mucous membranes, and wounds.

Other non-limiting examples of suitable carriers include petrolatum-based ointments, polyethylene glycol-based ointments and gels, poloxamer based ointments and gels, anhydrous compositions, aqueous based compositions, non-aqueous based compositions, hydrophobic compositions, and/or hydrophilic compositions.

The compositions of the invention may further comprise functional ingredients and adjuvants suitable for use in compositions for application to biological surfaces and/or non-biological surfaces. Non-limiting examples include absorbents, super absorbents, additional antibacterial agents, antioxidants, binders, buffering agents including Tris buffer solutions, bulking agents, chelating agents (preferably those that do not inhibit enzymatic activity), colorants, biocides, deodorant agents, additional enzymes, emulsion stabilizers, film formers, fragrance ingredients, humectants, lytic agents, enzymatic agents, opacifying agents, oxidizing agents, pH adjusters, plasticizers, preservatives, reducing agents, emollient skin conditioning agents, humectant skin conditioning agents such as glycerin and propylene glycol, moisturizers, surfactants, emulsifying agents, cleansing agents, foaming agents, hydrotopes, solvents, suspending agents, viscosity control agents (rheology modifiers), viscosity increasing agents (thickeners) including non-ionic cellulose derivatives such as hydroxyethylcellulose, preservatives such as methylparaben and propylparaben, salts such as sodium chloride and calcium chloride, and/or propellants. Listings and monographs of suitable functional ingredients are disclosed in McCutcheon's Vol. 1 Emulsifiers & Detergents, and Vol. 2 Functional Materials, 2001, herein incorporated by reference.

The compositions of the invention can further comprise additional pharmaceutically active ingredients, cosmetically active ingredients, vulnerary agents, wound healing agents, anti-fungal agents, antiseptics, cleansing agents, and additional antibacterial agents and antibiotics. The compositions can be sterile or preserved with antimicrobial preservatives.

The compositions of the present invention can be packaged in any suitable package configuration. Non-limiting examples include bottles, lotion pumps, toddles, tubes, jars, non-aerosol pump sprayers, aerosol containers, pouches, and/or packets. The packages may be configured for single-use or multiple-use administration.

D. Manufacture

The compositions of the invention may be manufactured by methods and equipment known in the art for manufacture of pharmaceutical and topical products, and products designed for application to non-biological surfaces, such as medical devices. Such methods include, but are not limited to the use of mechanical mixers including LIGHTNIN propeller mixers; COWLES dissolvers; SILVERSON dispersers; counter-rotating side-scrapping mixers; homogenizers and dispersers, including in-line or in-tank rotor-stator homogenizers; and mills, including 3-roll mills, ointment mills, or rotor-stator mills. "All-in-one" vacuum mixing systems that have a rotating side-scrapping mixer plus an in-tank homogenizer may also be used. Such mixers include, but are not limited to OLSA mixers, FRYMA-KORUMA mixers, and LEE TRI-MIX TURBO-SHEAR kettles. The compositions of the invention can be manufactured from small laboratory scale batches to full-scale production batches.

II. Bacterial Biofilms

The compositions of the invention are suitable for the reduction and/or elimination of both gram-positive and gram-negative bacterial biofilms on biological and non-biological surfaces. The compositions can also be used to prevent such biofilm formation on non-biological surfaces such as medical devices. The bacterial biofilms can contain more than one species of bacteria. The bacterial biofilms can comprise at least one gram-positive bacterial species. The bacterial biofilms can comprise at least one gram-negative bacterial species. The bacterial biofilms can comprise at least one gram-positive bacterial species and at least one gram-negative bacterial species. Non-limiting examples of gram-positive bacteria include *Staphylococcus* spp., such as *Staphylococcus aureus*, methicillin resistant *Staphylococcus aureus* (MRSA), and *Staphylococcus epidermidis*; *Streptococcus* spp., such as *Streptococcus pneumonia*; *Bacillus* spp.; *Listeria monocytogenes*; *Enterococcus* spp.; and lactic acid bacteria, such as *Lactobacillus plantarum* and *Lactococcus lactis*. Non-limiting examples of gram-negative bacteria include *Pseudomonas* spp., such as *Pseudomonas aeruginosa*; and *Escherichia coli*.

A. In-Vitro Biofilm Model

Suitable in-vitro biofilm models are available in the art. One such model useful to evaluate the biofilm efficacy of the compositions of the invention against bacterial biofilms is described herein. Bacteria are spotted onto a collagen matrix resting on a filter on a blood agar plate and incubated to allow biofilm formation. The model mimics in-vivo wound biofilms in that nutrients are provided from below the biofilm while topical treatments are applied at the air interface above. This in-vitro model and methodology is disclosed in the poster presentation, A Versatile In Vitro Biofilm Model Using Two Wound Pathogens to Screen Formulations, Van der Kar, et al., presented at the 2010 Wound Healing Society Annual Meeting, Poster BRC09, on Apr. 18, 2010 in Orlando, Fla., and is herein incorporated by reference. Further in-vitro biofilm models and methodologies are disclosed in the Examples below and also disclosed in the following publications, all of which are herein incorporated by reference: Penetration of Rifampin through *Staphylococcus epidermidis* Biofilms, Zheng, et al., Antimicrobial Agents and Chemotherapy, March 2002, p. 900-903; Oxygen Limitation Contributes to Antibiotic Tolerance of *Pseudomonas aeruginosa* in Biofilms, Borriello et al., Antimicrobial Agents and Chemotherapy, July 2004, p. 2659-2664; and Heterogeneity in *Pseudomonas aeruginosa* Biofilms Includes Expression of Ribosome Hibernation Factors in the Antibiotic-Tolerant Subpopulation and Hypoxia-Induced Stress Response in the Metabolically Active Population, Williamson et al., Journal of Bacteriology, February 2012, p. 2062-2073.

III. Methods of Use and Treatment

The compositions of the invention are useful for the reduction of bacteria in and/or elimination of bacterial biofilms on biological and non-biological surfaces, and are also useful for treatment of wounds, skin lesions, mucous membrane lesions, and other biological surfaces infected or contaminated with bacterial biofilms. The compositions can also be used to prevent biofilm growth or formation on surfaces susceptible of growing or forming biofilms (e.g., a surface of a medical device). Methods of reducing or eliminating a bacterial biofilm on a biological and/or non-biological surface comprise directly administering onto the biological and/or non-biological surface a composition comprising a combination of thermolysin and an aminoglycoside antibacterial agent. Methods of treating a wound, mucous membrane lesion, skin lesion, or other biological surface infected or contaminated with a bacterial biofilm comprise administering to the wound, mucous membrane lesion, skin lesion, or biological surface a composition comprising a combination of thermolysin and an aminoglycoside antibacterial agent, wherein the bacterial biofilm is reduced or eliminated. In preferred embodiments, the aminoglycoside antibacterial agent is a 4,6-disubstituted deoxystreptamine aminoglycoside. In a preferred embodiment, the 4,6-disubstituted deoxystreptamine aminoglycoside is gentamicin or gentamicin sulfate.

Other methods of the invention include combination therapy methods where a separate composition of thermolysin is used in conjunction with a separate composition of an aminoglycoside antibacterial agent. These methods are suitable for reducing or eliminating a bacterial biofilm on a wound, mucous membrane lesion, skin lesion, or other biological surface. Methods for reducing or eliminating a bacterial biofilm on a wound, mucous membrane lesion, skin lesion, or other biological surface comprise administering to the biological surface a first composition comprising thermolysin and a second composition comprising an aminoglycoside antibacterial agent, wherein the first and second compositions are combined. Methods of treating a wound, mucous membrane lesion, skin lesion, or other biological surface infected or contaminated with a bacterial biofilm comprise administering to the wound, mucous membrane lesion, skin lesion, or biological surface a first composition comprising thermolysin and a second composition comprising an aminoglycoside antibacterial agent, wherein the first and second compositions are combined, and wherein the bacterial biofilm is reduced or eliminated. In some embodiments, the first and second compositions are combined prior to administration to the surface. In other embodiments, the first and second compositions are combined after administration to the surface. The first and second compositions can be combined using techniques known is the art, e.g., mixing or spatulating. For example, a spatula or gloved finger can mix the first and second compositions together in a container prior to administration, or mix the compositions together directly on the surface after administration of the compositions. In another example, the first and second compositions can be combined on a gauze, bandage, or wound covering and placed on the surface such that the combined compositions come in contact with the surface. In some embodiments, the first composition is administered to the surface followed by the administration of the second composition. In other embodiments, the second composition is administered to the surface followed by the administration of the first composition. In still other embodiments, the first and second compositions are administered to the surface simultaneously. In some embodiments, the concentrations of thermolysin and the aminoglycoside antibacterial agent are at amounts effective to reduce or eliminate a bacterial biofilm on a biological surface when the first and second compositions are combined. In some embodiments, the combination of the first and second compositions exhibits synergistic antibacterial activity against a biofilm on a biological surface. In preferred embodiments, the aminoglycoside antibacterial agent is a 4,6-disubstituted deoxystreptamine aminoglycoside. In a preferred example, the 4,6-disubstituted deoxystreptamine aminoglycoside is gentamicin or gentamicin sulfate. In some embodiments, the first composition comprises thermolysin, but does not contain an aminoglycoside antibiotic agent. In some embodiments, the second composition comprises an aminoglycoside antibiotic agent, but does not contain thermolysin.

The embodiments disclosed herein of the compositions of the invention (i.e., the compositions comprising thermolysin and an aminoglycoside antibacterial agent) can also apply to the first and second compositions accordingly. These embodiments include those that relate to the various aminoglycoside antibacterial agents, the concentrations of thermolysin and aminoglycoside antibacterial agents, the carriers, adjuvants, packaging, and manufacture. The first and second compositions can comprise an acceptable carrier such as a carrier suitable for application to biological surfaces including wounds, mucous membranes, skin, organs and other biological tissues. The carrier can be a pharmaceutically acceptable carrier. The carrier can be a carrier suitable for topical administration and treatment. Non-limiting examples of carriers include lotions, solutions, suspensions, liquids, emulsions, creams, gels, ointments, pastes, aerosol sprays, aerosol foams, non-aerosol sprays, non-aerosol foams, films, powders, and sheets. Other non-limiting examples of suitable carriers include petrolatum-based ointments, polyethylene glycol-based ointments and gels, poloxamer based ointments and gels, anhydrous compositions, aqueous based compositions, non-aqueous based compositions, hydrophobic compositions, and/or hydrophilic compositions. The first and second compositions can be impregnated in or on the surface of gauzes, bandages, or other wound and skin dressing materials. The first and second compositions can further comprise functional ingredients, additional active ingredients, and adjuvants suitable for use in compositions for application to biological surfaces. The first and second compositions can be sterile or preserved with antimicrobial preservatives. The first and second compositions may be packaged in any suitable package configuration. Non-limiting examples include bottles, lotion pumps, toddles, tubes, jars, non-aerosol pump sprayers, aerosol containers, pouches, and/or packets. The packages may be configured for single-use or multiple-use administration. The first and second compositions can be packaged into a dual compartment container that keeps the two compositions separated during storage.

Subsequently following administration of the compositions of the invention or combination therapy, other compositions comprising pharmaceutically active ingredients, cosmetically active ingredients, vulnerary agents, wound healing agents, antibiotics, anti-fungal agents, antiseptic agents, cleansing agents, and/or antibacterial agents, can be administered to the wound, mucous membrane lesion, skin lesion, or biological surface for further treatment.

A. Biological Surfaces

The compositions of the invention are useful for reducing or eliminating a bacterial biofilm on a biological surface by administering the compositions directly onto the biological surface. Non-limiting examples of biological surfaces include wounds (including chronic wounds, acute wounds, and burns), skin lesions, skin, mucous membranes, mucous membrane lesions, internal organs, body cavity, oral cavity, bone tissue, muscle tissue, nerve tissue, ocular tissue, urinary tract tissue, lung and trachea tissue, sinus tissue, ear tissue, dental tissue, gum tissue, nasal tissue, vascular tissue, cardiac tissue, epithelium, and epithelial lesions, and peritoneal tissue. Non-limiting examples of chronic wounds include diabetic foot ulcers, venous ulcers, arterial ulcers, decubitus ulcers, stasis ulcers, and pressure ulcers. Non-limiting examples of acute wounds include cuts and surgical wounds. Non-limiting examples of skin lesions and mucous membrane lesions include blisters, ulcers, abrasions, warts, abscesses, scrapes, and skin and mucosal infections such as staph or MRSA infections. Examples of skin lesions and mucous membrane lesions are disclosed in "Description of Skin Lesions", MacNeal, Robert J., the on-line Merck Manual Professional Version, March 2013, http://www.merckmanuals.com/professional/dermatologic-disorders/approach-to-the-dermatologic-patient/description-of-skin-lesions herein incorporated by reference. Skin lesions can appear on the epidermis, lips, ear canal, scalp, cuticle, nail bed, or genitalia. Mucous membrane lesions can appear on the oral mucosa, nasal mucosa, penile and vaginal mucosa, or anus.

B. Topical Treatment of Wounds

The compositions of the invention are useful for the treatment of wounds (including chronic wounds, acute wounds, and burns) infected or contaminated with bacterial biofilms, by topically administering the compositions to the wound. Non-limiting examples of chronic wounds include diabetic foot ulcers, venous ulcers, arterial ulcers, decubitus ulcers, stasis ulcers, and pressure ulcers. Non-limiting examples of acute wounds include cuts and surgical wounds. In some embodiments, the wound has eschar and/or necrotic tissue and is in need of debridement. In other embodiments, the wound does not have eschar and/or necrotic tissue and is not in need of debridement.

Because the compositions of the invention contain thermolysin, a proteolytic enzyme, the compositions can also serve a dual function and debride wounds that are in need of debridement in addition to reducing or eliminating a bacterial biofilm present in the wounds. Thus, in one aspect of the invention, disclosed is a method for treating a wound infected or contaminated with a bacterial biofilm and in need of debridement, the method comprising topically administering to the wound a composition comprising a combination of thermolysin and an aminoglycoside antibacterial agent; wherein the bacterial biofilm is reduced or eliminated; and wherein the wound is debrided. In some embodiments, the concentrations of thermolysin and the aminoglycoside antibacterial agent are at amounts effective to reduce or eliminate a bacterial biofilm in a wound infected or contaminated with the bacterial biofilm. In some embodiments, the concentration of thermolysin is at an amount effective to debride a wound in need of debridement. In some embodiments, the combination of thermolysin and the aminoglycoside antibacterial agent exhibits synergistic antibacterial activity against a bacterial biofilm in a wound infected or contaminated with the bacterial biofilm. In preferred embodiments, the aminoglycoside antibacterial agent is a 4,6-disubstituted deoxystreptamine aminoglycoside. In a preferred embodiment, the 4,6-disubstituted deoxystreptamine aminoglycoside is gentamicin or gentamicin sulfate. In another aspect of the invention, disclosed is a method of treating a wound infected or contaminated with a bacterial biofilm and in need of debridement, the method comprising topically administering to the wound a first composition comprising thermolysin and a second composition comprising an aminoglycoside antibacterial agent, wherein the first and second compositions are combined, wherein the bacterial biofilm is reduced or eliminated, and wherein the wound is debrided. In some embodiments, the first and second compositions are combined prior to administration to a wound. In other embodiments, the first and second compositions are combined after administration to a wound. In some embodiments, the concentrations of thermolysin and the aminoglycoside antibacterial agent are at amounts effective to reduce or eliminate a bacterial biofilm on a wound when the first and second compositions are combined. In some embodiments, the concentration of thermolysin is at an amount effective to debride a wound in need of debridement. In some embodiments, the combination of the first and second compositions exhibits synergistic antibacterial activity against a biofilm on a wound infected or contaminated with the bacterial biofilm. In preferred embodiments, the aminoglycoside antibacterial agent is a 4,6-disubstituted deoxystreptamine aminoglycoside.

C. Topical Treatment of Skin Lesions and Mucous Membrane Lesions

The compositions of the invention are useful for the treatment of skin lesions or mucous membrane lesions infected or contaminated with bacterial biofilms by topically administering the compositions to the skin lesion or mucous membrane lesions. Non-limiting examples of skin lesions and mucous membrane lesions include blisters, ulcerations, abrasions, warts, abscesses, scrapes, and skin and mucosal infections such as staph or MRSA infections. Skin lesions can appear on the epidermis, lips, ear canal, scalp, cuticle, nail bed, or genitalia. Mucous membrane lesions can appear on the oral mucosa, nasal mucosa, penile and vaginal mucosa, or anus. In some embodiments, the mucous membrane lesion or skin lesion includes eschar and/or necrotic tissue and is in need of debridement. In various embodiments, the compositions serve a dual function and further debride lesions that are in need of debridement in addition to reducing or eliminating a bacterial biofilm present in the lesions. In other embodiments, the mucous membrane lesion or skin lesion does not include eschar and/or necrotic tissue and is not in need of debridement.

Because the compositions of the invention contain thermolysin, a proteolytic enzyme, the compositions can also serve a dual function and debride mucous membrane lesions or skin lesions that are in need of debridement in addition to reducing or eliminating a bacterial biofilm present in the mucous membrane lesions or skin lesions. Thus, in one aspect of the invention, disclosed is a method for treating a mucous membrane lesion or skin lesion infected or contaminated with a bacterial biofilm and in need of debridement, the method comprising topically administering to the mucous membrane lesion or skin lesion a composition comprising a combination of thermolysin and an aminoglycoside antibacterial agent; wherein the bacterial biofilm is reduced or eliminated; and wherein the mucous membrane lesion or skin lesion is debrided. In some embodiments, the concentrations of thermolysin and the aminoglycoside antibacterial agent are at amounts effective to reduce or eliminate a bacterial biofilm in a mucous membrane lesion or skin lesion infected or contaminated with the bacterial biofilm. In some embodiments, the concentration of thermolysin is at an amount effective to debride a mucous membrane lesion or skin lesion in need of debridement. In some embodiments, the combination of thermolysin and the aminoglycoside antibacterial agent exhibits synergistic antibacterial activity against a bacterial biofilm in a mucous membrane lesion or skin lesion infected or contaminated with the bacterial biofilm. In preferred embodiments, the aminoglycoside antibacterial agent is an aminoglycoside antibacterial agent having 4,6-disubstituted deoxystreptamine. In a preferred embodiment, the aminoglycoside antibacterial agent having 4,6-disubstituted deoxystreptamine is gentamicin or gentamicin sulfate. In another aspect of the invention, disclosed is a method of treating a mucous membrane lesion or skin lesion infected or contaminated with a bacterial biofilm and in need of debridement, the method comprising topically administering to the mucous membrane lesion or skin lesion a first composition comprising thermolysin and a second composition comprising an aminoglycoside antibacterial agent, wherein the first and second compositions are combined, wherein the bacterial biofilm is reduced or eliminated, and wherein the mucous membrane lesion or skin lesion is debrided. In some embodiments, the first and second compositions are combined prior to administration to a mucous membrane lesion or skin lesion. In other embodiments, the first and second compositions are combined after administration to a mucous membrane lesion or skin lesion. In some embodiments, the concentrations of thermolysin and the aminoglycoside antibacterial agent are at amounts effective to reduce or eliminate a bacterial biofilm on a mucous membrane lesion or skin lesion when the first and second compositions are combined. In some embodiments, the concentration of thermolysin is at an amount effective to debride a mucous membrane lesion or skin lesion in need of debridement. In some embodiments, the combination of the first and second compositions exhibits synergistic antibacterial activity against a biofilm on a mucous membrane lesion or skin lesion infected or contaminated with the bacterial biofilm. In preferred embodiments, the aminoglycoside antibacterial agent is a 4,6-disubstituted deoxystreptamine aminoglycoside.

D. Treatment of Other Biological Surfaces

The compositions of the invention are useful for the treatment of other biological surfaces infected or contaminated with bacterial biofilms by administering the compositions to the biological surface. Non-limiting examples of other biological surfaces include internal organs, body cavity, oral cavity, bone tissue, muscle tissue, nerve tissue, ocular tissue, urinary tract tissue, lung tissue, trachea tissue, sinus tissue, ear tissue, dental tissue, gum tissue, nasal tissue, vascular tissue, cardiac tissue, epithelium tissue, epithelial lesions, vaginal tissue, and/or peritoneal tissue.

E. Non-Biological Surfaces

The compositions of the invention are useful for reducing or eliminating a bacterial biofilm on a non-biological surface, such as the surface of an article of manufacture such as a medical device, by administering the compositions to the non-biological surface. The compositions can also be used to prevent biofilm growth or formation on these non-biological surfaces. Such surfaces can be susceptible to biofilm growth or formation due to their exposure to human tissue and/or wounds. Non-limiting examples of medical devices include urinary tract prostheses; urinary tract catheters, peritoneal membrane catheters, peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses; percutaneous sutures; and tracheal and ventilator tubing.

The surface of an article of manufacture, including medical devices, can be coated with the compositions of the inventions in order to prevent the formation of bacterial biofilms on the surface of the article of manufacture. In some embodiments, a bacterial biofilm is not present on the surface prior to coating. In other embodiments, a bacterial biofilm is present on the surface prior to coating.

IV. Kits

Disclosed are kits comprising (a) a first composition comprising thermolysin, and (b) a second composition comprising an aminoglycoside antibacterial agent. In preferred embodiments, the aminoglycoside antibacterial agent in the second composition is a 4,6-disubstituted deoxystreptamine aminoglycoside. In a preferred embodiment, the 4,6-disubstituted deoxystreptamine aminoglycoside is gentamicin or gentamicin sulfate. In some embodiments, the kit further comprises instructions for administering the first and second compositions to a biological surface, wound, mucous membrane lesion, and/or skin lesion infected or contaminated with a bacterial biofilm. In some embodiments, the instructions include combining the first and second compositions. In other embodiments, the wound, mucous membrane lesion, and/or skin lesion is further in need of debridement.

The first and second compositions can each comprise an acceptable carrier such as a carrier suitable for application to biological surfaces including wounds, mucous membranes, skin, organs and other biological tissues. The carrier can be a pharmaceutically acceptable carrier. The carrier can be a carrier suitable for topical administration and treatment. Non-limiting examples of carriers include lotions, solutions, suspensions, liquids, emulsions, creams, gels, ointments, pastes, aerosol sprays, aerosol foams, non-aerosol sprays, non-aerosol foams, films, powders, and sheets. Other non-limiting examples of suitable carriers include petrolatum-based ointments, polyethylene glycol-based ointments and gels, poloxamer based ointments and gels, anhydrous compositions, aqueous based compositions, non-aqueous based compositions, hydrophobic compositions, and/or hydrophilic compositions. The first and second compositions can further comprise functional ingredients, additional active ingredients, and adjuvants suitable for use in compositions for application to biological surfaces. The compositions can be sterile or preserved with antimicrobial preservatives. The first and second compositions may be packaged in any suitable package configuration. Non-limiting examples include bottles, lotion pumps, toddles, tubes, jars, non-aerosol pump sprayers, aerosol containers, pouches, and/or packets. The packages may be configured for single-use or multiple-use administration. The first and second compositions can be packaged into a dual compartment container that keeps the two compositions separated during storage.

EXAMPLES

Example 1: In-Vitro Gram-Positive Bacterial Biofilm Study with Thermolysin and Collagenase An in-vitro assay was performed to determine the bacterial biofilm reduction capabilities of thermolysin and collagenase on gram-positive bacterial biofilms. In this assay, S. aureus ATCC 6538 was suspended in a growth media of tryptic soy broth supplemented with 0.25% glucose for optimal bacterial biofilm formation. The suspension was transferred to the wells of sterile 96 well plates and incubated for 22 hours at 37° C. with one change of media. After formation of the bacterial biofilm, the growth media was replaced with solutions of thermolysin dissolved in growth media at various concentrations in some wells and replaced with solutions of collagenase dissolved in growth media at the same concentrations in other wells (enzyme concentrations were 0.000001 mg/mL, 0.00001 mg/mL, 0.0001 mg/mL, 0.001 mg/mL, 0.01 mg/mL, 0.1 mg/mL, 1.0 mg/mL, and 10 mg/mL). After 16 hours, the remaining attached bacteria were quantified by aspirating the enzyme solutions (enzyme+growth media) and washing the plate thoroughly followed by crystal violet staining and recording the absorbance at 570 nm. A growth media control without enzyme was also tested. The crystal violet binds to negative charges on the remaining attached bacteria and the EPS. A decreased absorbance compared to the Control indicates a reduction of attached bacteria meaning a reduction of the bacterial biofilm occurred. FIG. 1 provides a summary of these data. As illustrated in FIG. 1, thermolysin had an effect in reducing the bacterial biofilm at concentrations of 0.00001 mg/mL-10 mg/mL.

Figure 2:
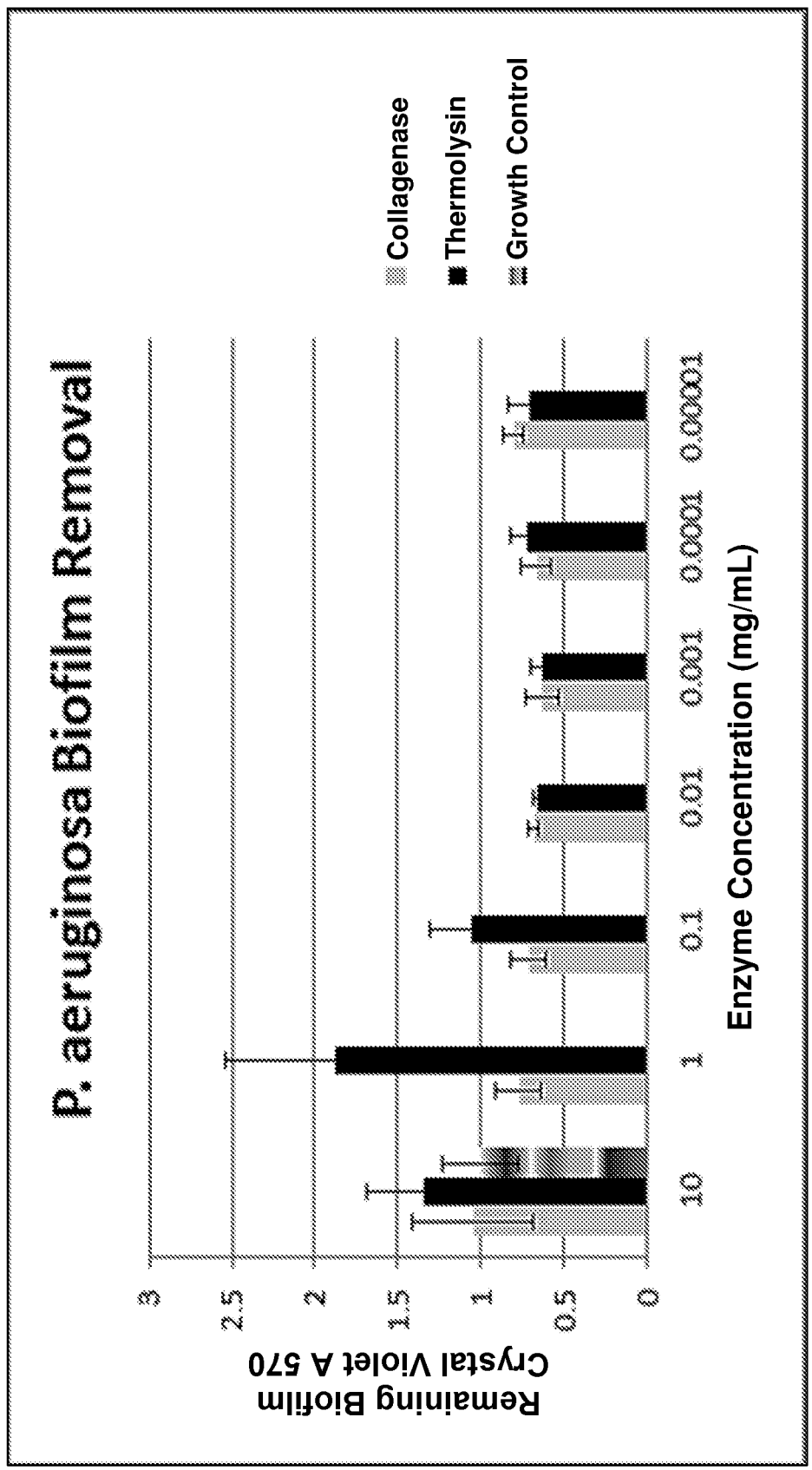
FIG. 2. A graph showing the effect of thermolysin and collagenase on a P. aeruginosa bacterial biofilm in-vitro.

Example 2: In-Vitro Gram-Negative Bacterial Biofilm Study with Thermolysin and Collagenase An in-vitro assay was performed to determine the bacterial biofilm reduction capabilities of thermolysin and collagenase on gram-negative bacterial biofilms. In this assay P. aeruginosa ATCC15442 was suspended in a growth media of 10% tryptic soy broth in PBS supplemented with 0.45% glucose (TSBG). The suspension was transferred to the wells of sterile 96 well plates and incubated for 18 hours at 37° C., then the media was changed with fresh media and incubated an additional 8 hours at 37° C. After formation of the bacterial biofilm, the growth media was replaced with solutions of thermolysin dissolved in TSBG growth media at various concentrations in some wells and replaced with solutions of collagenase dissolved in growth media at the same concentrations in other wells (enzyme concentrations were 0.00001 mg/mL, 0.0001 mg/mL, 0.001 mg/mL, 0.01 mg/mL, 0.1 mg/mL, 1.0 mg/mL, and 10 mg/mL). After 18 hours at 37° C., the remaining attached bacteria were quantified by removing the enzyme solutions (enzyme+ TSBG growth media) and washing the plate thoroughly followed by crystal violet staining and recording the absorbance at 570 nm. A growth media control without enzyme was also tested. The crystal violet binds to negative charges on the remaining attached bacteria and the EPS. A decreased absorbance compared to the Control indicates a reduction of attached bacteria meaning a reduction of the bacterial biofilm occurred. FIG. 2 provides a summary of these data. As illustrated in FIG. 2, thermolysin had little effect in reducing the bacterial biofilm at concentrations of 0.00001 mg/mL-0.01 mg/mL, and no effect in reducing the bacterial biofilm at concentrations of 0.1 mg/mL-10 mg/mL.

Example 3: MIC Values of Gentamicin Sulfate and Gentamicin Sulfate Plus Thermolysin for Gram-Positive and Gram-Negative Bacteria The minimum inhibitory concentration (MIC) values of gentamicin sulfate and gentamicin sulfate plus thermolysin for S. aureus and P. aeruginosa suspensions were generated and are shown in Table 2. The concentration of thermolysin in the MIC experiments was kept constant at 50 μg/mL.

TABLE 2

MIC values

| Strain | Gentamicin sulfate (μg/mL) | | Gentamicin sulfate plus thermolysin (μg/mL) | |
| --- | --- | --- | --- | --- |
| | Rep 1 | Rep 2 | Rep 1 | Rep 2 |
| S. aureus ATCC 29213 | 1.6 | 1.6 | 1.6 | 1.6 |
| P. aeruginosa ATCC 27312 | 50 | 50 | 50 | 50 |

As can be seen with the MIC values in Table 2, the addition of thermolysin to gentamicin sulfate did not affect the MIC of gentamicin sulfate for S. aureus or P. aeruginosa bacteria.

Example 4: Formulations

The following test formulations shown in Table 3 were prepared.

TABLE 3

Test Formulations

| Component (% w/w) | Formula A: placebo | Formula B: 0.8% thermolysin + 0.7% genta | Formula C: 0.7% gentamicin | Formula D: 0.8% thermolysin |
| --- | --- | --- | --- | --- |
| Hydroxyethylcellulose (HEC) (NATROSOL ™ 250 HX Pharma) | 2.62 | 2.72 | 2.69 | 2.60 |
| Thermolysin | — | 0.80 | — | 0.80 |
| Gentamicin Sulfate USP | — | 0.70* | 0.70* | — |
| Sodium Chloride | 0.27 | 0.27 | 0.27 | 0.27 |
| Calcium Chloride | 0.10 | 0.10 | 0.10 | 0.10 |
| Methylparaben | 0.23 | 0.23 | 0.25 | 0.25 |
| Propylparaben | 0.05 | 0.05 | 0.05 | 0.05 |
| Propylene Glycol | 13.7 | 14.1 | 13.0 | 13.6 |
| Tris Buffer Solution, 17 mM, pH = 7.5 | q.s. ad 100% | q.s. ad 100% | q.s. ad 100% | q.s. ad 100% |

*equivalent to 0.42% w/w gentamicin

Note:
The 0.70% of gentamicin sulfate USP shown in the test formulations of Table 3 is the actual concentration of gentamicin sulfate as-is in the formulations which is equivalent to 0.42% w/w gentamicin. Procedure: The methylparaben, proplyparaben, and propylene glycol were dissolved in the Tris buffer solution at 70° C. The solution was cooled to room temperature and the HEC was added and mixed. Then the thermolysin (if present), gentamicin sulfate (if present), sodium chloride, and calcium chloride were added and mixed until uniform. A gel was formed in each formula.

A preferred example of a composition of the invention is test Formula B: "0.8% thermolysin+0.7% genta" shown in Table 3, which contains 0.80% w/w thermolysin and 0.70% w/w gentamicin sulfate USP (as-is basis) equivalent to 0.42% w/w gentamicin.

Example 5: In-Vitro S. aureus Biofilm Model Using Test Formulations from Table 3

Bacterial Strain: Staphylococcus aureus ATCC 6538 was grown overnight onto Trypticase Soy Agar II (TSAII)+5% sheep's blood at 37° C.

Simulated Wound Fluid: A simulated would fluid (SWF) was prepared containing 1× Hank's Balanced Salt Solution (with calcium, magnesium, and dextrose) supplemented with 2% FBS.

Biofilm Assemblies: Biofilm assemblies were comprised of 13 mm PORETICS™ Polycarbonate Track etched Black 0.2 μm membrane disks with a 4 mm punch of a PROMOGRAN™ collagen wound matrix dressing applied to the center of the membrane disk. The assemblies were aseptically put together on the surface of a TSAII+5% sheep's blood plate with up to 9 assemblies per plate.

Inoculation and Biofilm Establishment: The S. aureus colonies were resuspended in 1× Phosphate Buffered Saline from the overnight plate to an absorbance of 0.1 at 600 nm (~8.0 log cfu/mL). The S. aureus biofilms were inoculated by pipetting 2 μL of the inoculum onto the center of the PROMOGRAN punch with an approximate concentration of log 5.0 cfu/mL. At the end of the incubation period the recovered biofilm counts for *S. aureus* were approximately 8.0 log cfu/sample indicating the successful establishment of a biofilm.

Biofilm Treatments: 0.25 g of each test formulation in Table 3 was applied using a syringe to 13 mm sterile TELFA™ swatches which were wetted with 450 μL of Simulated Wound Fluid (SWF). The treatments were placed in direct contact with the biofilms (the test formulation was in direct contact the biofilms with the TELFA swatch on top) and gently tamped down to ensure consistent contact. The plates were further incubated for 24 hours at 37° C. A moist control was run to serve as reference point and was treated with SWF wetted TELFA swatches only.

Biofilm Recoveries: At the end of treatment, biofilm assemblies were individually recovered whole into 5 mL of DE Neutralizing Broth and vortexed at maximum speed for 2 minutes to remove the biofilm and neutralize any active antimicrobial agent (note: the confirmation of biofilm counts prior to the start of treatment was performed in this manner).

Colony Count Determination: The resuspended biofilms were then serially diluted in an 8 point 1:10 dilution series and 10 μL was spot plated on charcoal agar (which will bind and inactivate drugs and any remaining antimicrobial agents) and grown overnight at 37° C. Colony counts were performed the next day and the count determined from dilutions that had between 1-30 colonies. In the case of multiple dilutions that had colony counts that fell with the 1-30 counts, the least diluted count was accepted for the final count.

Data Analysis: Colony counts were converted into colony counts/sample, then to log colony counts/sample. Log reductions versus the moist control were determined by subtracting the treatment log cfu/sample from the mean log cfu/sample of the moist control group.

Figure 3:
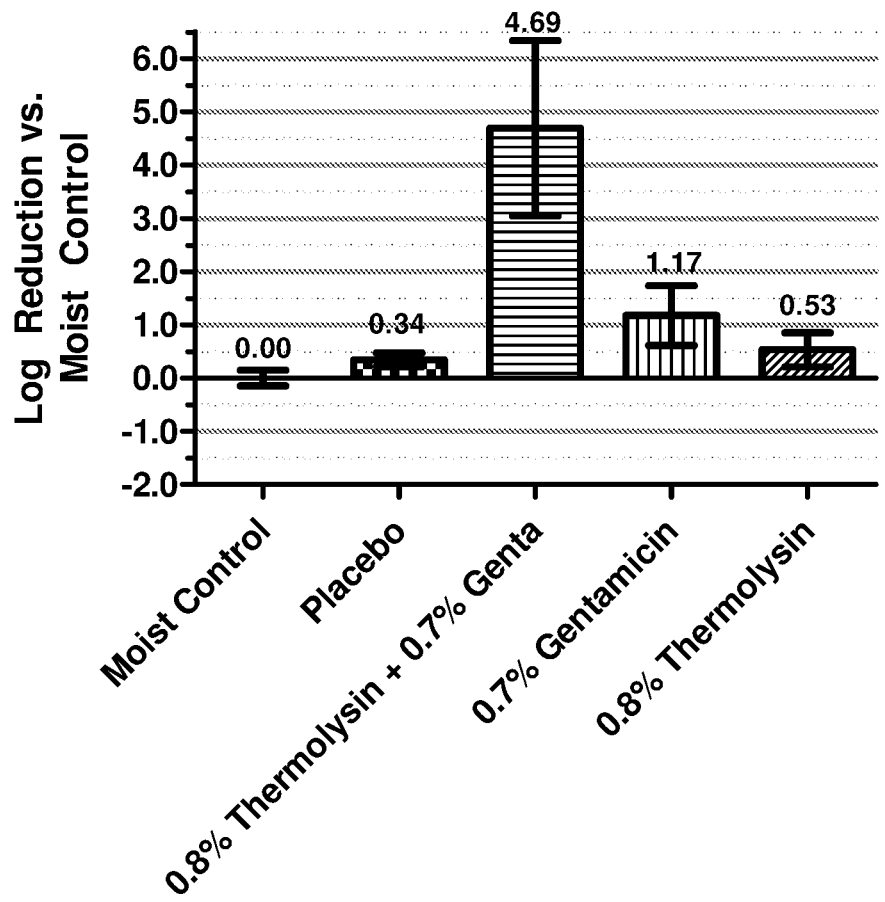
FIG. 3. A graph showing the log reduction of bacteria in a S. aureus bacterial biofilm in-vitro model treated with test formulations vs. moist control.

Results: The results of the *S. aureus* biofilm model study are shown in FIG. 3. Mean log reduction vs. moist control results are shown for each test formulation (error bars equal 95% confidence intervals with n=7-8 pooled from 2 independent studies). The cumulative log reduction effect of test Formula C (gentamicin) plus test Formula D (thermolysin) is less than the log reduction effect of test Formula B (gentamicin plus thermolysin). Test Formula B also has a greater log reduction effect than test Formula A (placebo) and moist control. Thus, the results indicate synergistic antibacterial activity by the combination of the of the aminoglycoside antibacterial agent and thermolysin against gram-positive bacterial biofilms.

Example 6: In-Vitro *P. aeruginosa* Biofilm Model Using Test Formulations from Table 3

Bacterial Strain: *P. aeruginosa* ATCC 27312 was grown overnight on Trypticase Soy Agar at 37° C. two days prior to the start of the study. The day before the study, a single colony was sub-cultured into Trypticase Soy Broth, then grown at 37° C. overnight with shaking (100 rpm).

Simulated Wound Fluid: A simulated would fluid (SWF) was prepared containing 1× Hank's Balanced Salt Solution (with calcium, magnesium, and dextrose) supplemented with 2% FBS.

Biofilm Assemblies: Biofilm assemblies were comprised of 13 mm PORETICS Polycarbonate Track etched Black 0.2 μm membrane disks with a 4 mm punch of a PROMOGRAN® collagen wound matrix dressing applied to the center of the membrane disk. The assemblies were aseptically put together on the surface of a TSAII+5% sheep's blood plate with up to 9 assemblies per plate.

Inoculation and Biofilm Establishment: The overnight broth culture of *P. aeruginosa* was diluted to an absorbance of 0.1 at 600 nm (~8.0 log cfu/mL) in Trypticase Soy Broth (inoculum). The *P. aeruginosa* biofilm assemblies were inoculated by pipetting 3 μL of the inoculum onto the center of the PROMOGRAN punch with an approximate concentration of log 5.5 cfu/mL. The biofilm plates were incubated for 24 hours at 37° C. to establish the biofilm prior to the start of treatment. At the end of the incubation period the recovered biofilm counts for *P. aeruginosa* were approximately 8.0 log cfu/sample indicating the successful establishment of a biofilm.

Biofilm Treatments: 0.25 g of each test formulation in Table 3 was applied using a syringe to 13 mm sterile TELFA swatches which were wetted with 450 μL of Simulated Wound Fluid (SWF). The treatments were placed in direct contact with the biofilms (the test formulation was in direct contact the biofilms with the TELFA swatch on top) and gently tamped down to ensure consistent contact. The plates were further incubated for 24 hours at 37° C. A moist control was run to serve as reference point and was treated with SWF wetted TELFA swatches only.

Biofilm Recoveries: At the end of treatment, biofilm assemblies were individually recovered whole into 5 mL of DE Neutralizing Broth and vortexed at maximum speed for 2 minutes to remove the biofilm and neutralize any active antimicrobial agent (note: the confirmation of biofilm counts prior to the start of treatment was performed in this manner).

Colony Count Determination: The resuspended biofilms were then serially diluted in an 8 point 1:10 dilution series and 10 μL was spot plated on charcoal agar (which will bind and inactivate drugs and any remaining antimicrobial agents) and grown overnight at 37° C. Colony counts were performed the next day and the count determined from dilutions that had between 1-30 colonies. In the case of multiple dilutions that had colony counts that fell with the 1-30 counts, the least diluted count was accepted for the final count.

Data Analysis: Colony counts were converted into colony counts/sample, then to log colony counts/sample. Log reductions versus the moist control were determined by subtracting the treatment log cfu/sample from the mean log cfu/sample of the moist control group.

Figure 4:
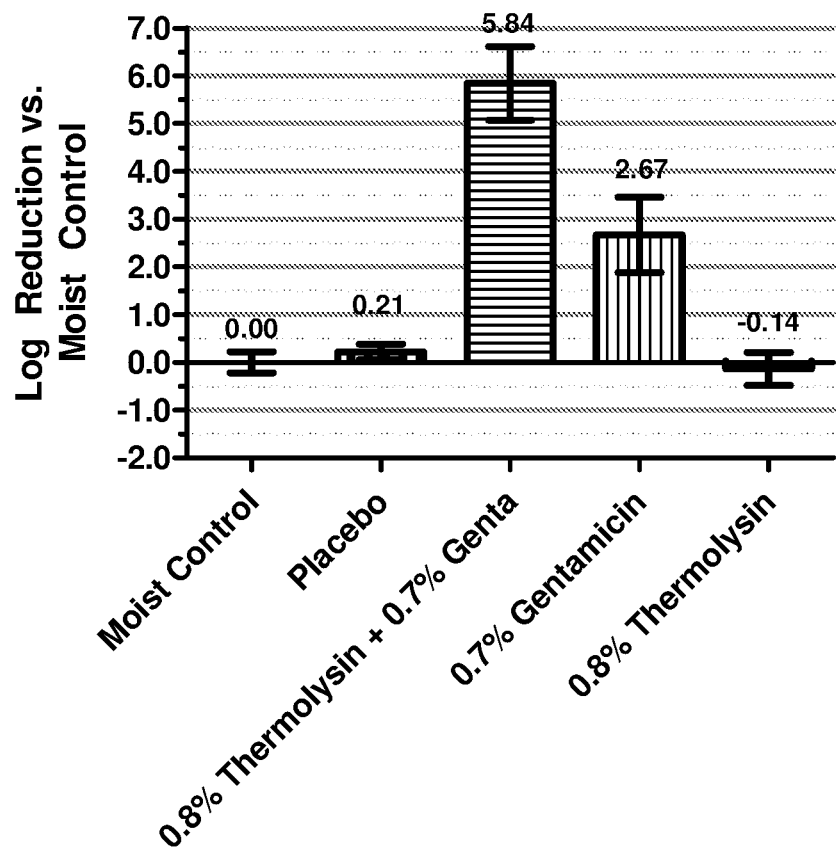
FIG. 4. A graph showing the log reduction of bacteria in a P. aeruginosa bacterial biofilm in-vitro model treated with test formulations vs. moist control.

Results: The results of the *P. aeruginosa* study are shown in FIG. 4. Mean log reduction vs. moist control results are shown for each test formulation (error bars equal 95% confidence intervals with n=7-8 pooled from 2 independent studies). The cumulative log reduction effect of test Formula C (gentamicin) plus test Formula D (thermolysin) is less than the log reduction effect of test Formula B (gentamicin plus thermolysin). Test Formula B also has a greater log reduction effect than test Formula A (placebo) and moist control. Thus, the results indicate synergistic antibacterial activity by the combination of the of the aminoglycoside antibacterial agent and thermolysin against gram-negative bacterial biofilms.

The invention claimed is:
1. A method of treating a biological surface infected or contaminated with a bacterial biofilm or reducing or eliminating a bacterial biofilm on a biological surface, the method comprising administering to the biological surface a composition comprising a combination of thermolysin and gentamicin or a salt form thereof, wherein the concentrations of thermolysin and gentamicin in the composition are at amounts effective to reduce or eliminate the bacterial biofilm on the biological surface.

2. The method of claim 1, wherein the gentamicin or the salt form thereof is gentamicin sulfate.

3. The method of claim 2, wherein the concentration of thermolysin is 0.1 to 1% w/w, based on the total weight of the composition, and the concentration of gentamicin sulfate is equivalent to a concentration of gentamicin of 0.1 to 1% w/w, based on the total weight of the composition.

4. The method of claim 1, wherein the composition further comprises a carrier suitable for application to a biological surface.

5. The method of claim 4, wherein the carrier is a lotion, solution, suspension, liquid, emulsion, cream, gel, ointment, paste, aerosol spray, aerosol foam, non-aerosol spray, non-aerosol foam, film, or sheet.

6. The method of claim 5, wherein the carrier is suitable for topical administration.

7. The method of claim 1, wherein the bacterial biofilm comprises at least one gram-positive bacterial species.

8. The method of claim 1, wherein the bacterial biofilm comprises at least one gram-negative bacterial species.

9. The method of claim 1, wherein the bacterial biofilm comprises at least one gram-positive bacterial species and at least one gram-negative bacterial species.

10. The method of claim 1, wherein the biological surface is a chronic wound, acute wound, or burn.

11. The method of claim 10, wherein the chronic wound is a diabetic foot ulcer, venous ulcer, arterial ulcer, decubitus ulcer, stasis ulcer, or pressure ulcer.

12. The method of claim 10, wherein the biological surface is in further need of debridement.

13. The method of claim 1, wherein the biological surface is a skin lesion or a mucous membrane lesion.

14. The method of claim 1, wherein the biological surface is an internal organ, a body cavity, an oral cavity, a bone tissue, a muscle tissue, a nerve tissue, an ocular tissue, a urinary tract tissue, a lung tissue, a trachea tissue, a sinus tissue, an ear tissue, a dental tissue, a gum tissue, a nasal tissue, a vascular tissue, a cardiac tissue, an epithelium tissue, an epithelial lesion, a vaginal tissue, or a peritoneal tissue.

* * * * *

UNITED STATES PATENT AND TRADEMARK OFFICE
CERTIFICATE OF CORRECTION

| | |
|---|---|
| PATENT NO. | : 11,413,300 B2 |
| APPLICATION NO. | : 16/481668 |
| DATED | : August 16, 2022 |
| INVENTOR(S) | : Aleksa Jovanovic et al. |

It is certified that error appears in the above-identified patent and that said Letters Patent is hereby corrected as shown below:

On the Title Page

<u>(57) Abstract, Line 3:</u>
Delete "as methods" and replace with -- as well as methods --.

Signed and Sealed this
Twenty-second Day of November, 2022

Katherine Kelly Vidal
*Director of the United States Patent and Trademark Office*